(12) United States Patent
Miyazawa et al.

(10) Patent No.: US 10,861,602 B2
(45) Date of Patent: Dec. 8, 2020

(54) MEDICAL IMAGING APPARATUS, INFORMATION PROCESSING METHOD, AND COMPUTER-READABLE STORAGE MEDIUM

(71) Applicant: CANON KABUSHIKI KAISHA, Tokyo (JP)

(72) Inventors: Nobu Miyazawa, Yokohama (JP); Koji Takekoshi, Fujisawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 4 days.

(21) Appl. No.: 16/279,821

(22) Filed: Feb. 19, 2019

(65) Prior Publication Data

US 2019/0189273 A1 Jun. 20, 2019

Related U.S. Application Data

(63) Continuation of application No. 14/818,110, filed on Aug. 4, 2015, now abandoned, which is a (Continued)

(30) Foreign Application Priority Data

Apr. 24, 2009 (JP) .................................. 2009-106730

(51) Int. Cl.
*G16H 40/63* (2018.01)
*G06T 1/00* (2006.01)
(Continued)

(52) U.S. Cl.
CPC ........... *G16H 40/63* (2018.01); *G06F 19/321* (2013.01); *G06T 1/0007* (2013.01); *G16H 30/20* (2018.01)

(58) Field of Classification Search
CPC .......................... G06F 19/3406; G06F 19/321
See application file for complete search history.

(56) References Cited

U.S. PATENT DOCUMENTS 6,763,238 B1 * 7/2004 Okano .............. H04W 52/0251
455/456.4
2004/0059756 A1 * 3/2004 Mochizuki ............ G06F 19/321
(Continued)

FOREIGN PATENT DOCUMENTS

JP     2007-215685     *  8/2007    ......... G06Q 30/0185

OTHER PUBLICATIONS

Noumeir, R., "Benefits of the DICOM Modality Performed Procedure Step", Journal of Digital Imaging, Dec. 2005, pp. 260-269, vol. 18, No. 4.

(Continued)

*Primary Examiner* — Rocio Del Mar Perez-Velez
*Assistant Examiner* — Olvin Lopez Alvarez
(74) *Attorney, Agent, or Firm* — Canon U.S.A., Inc., IP Division

(57) ABSTRACT

A medical imaging apparatus includes a transmission suspension time determination unit that determines a transmission suspension time from when an inspection is ended to when inspection end information generated by an inspection end information generation unit is transmitted to a hospital information system based on inspection information; an inspection end information transmission unit transmits the generated inspection end information to the hospital information system after the transmission suspension time has passed after the inspection is ended; and an additional imaging-operation instruction determination unit determines whether an additional imaging-operation instruction is issued from an operator before the transmission suspension time passes. If it is determined that the additional imaging-operation instruction is issued, inspection end information including a content of the imaging operation additionally executed according to the additional imaging operation instruction is executed, and the inspection end information (Continued)

including the content of the additional imaging-operation is transmitted.

12 Claims, 23 Drawing Sheets

Related U.S. Application Data continuation of application No. 14/160,255, filed on Jan. 21, 2014, now Pat. No. 9,129,049, which is a continuation of application No. 12/764,003, filed on Apr. 20, 2010, now abandoned.

(51) Int. Cl.
*G16H 30/20* (2018.01)
*G06F 19/00* (2018.01)

(56) References Cited

U.S. PATENT DOCUMENTS

| | | | | |
|---|---|---|---|---|
| 2005/0114175 | A1 | 5/2005 | O'Dea | |
| 2007/0083106 | A1* | 4/2007 | Sprung | G01R 33/56325 600/413 |
| 2007/0162260 | A1* | 7/2007 | Nordstrom | G06F 9/505 702/186 |
| 2008/0240533 | A1* | 10/2008 | Piron | G01R 33/482 382/131 |
| 2008/0279171 | A1* | 11/2008 | Kim | H04L 1/1685 370/346 |
| 2009/0167786 | A1* | 7/2009 | Stanions | G06T 3/4038 345/630 |
| 2010/0026830 | A1* | 2/2010 | Kim | G03B 17/00 348/222.1 |
| 2011/0199898 | A1* | 8/2011 | Cho | H04W 48/06 370/230 |
| 2013/0326068 | A1* | 12/2013 | Yen | H04L 67/16 709/226 |

OTHER PUBLICATIONS

Oosterwijk, H., et al., "Modality Interface DICOM Conformance Requirements", Final Version 1.2, Department of Veterans Affairs, Sep. 7, 1999, pp. 1-40.

Noumeir, R., "Radiology interpretation process modeling", Journal of Biomedical Informatics, 2006, pp. 103-114, vol. 39.

* cited by examiner

| INDEX SCORE TOTAL VALUE | TRANSMISSION SUSPENSION TIME (min) |
|---|---|
| 0~50 | 0 |
| 51~100 | 5 |
| 101~200 | 30 |
| 201~350 | 60 |
| 351~400 | 100 |
| 401~500 | 200 |
| 501~ | 360 |

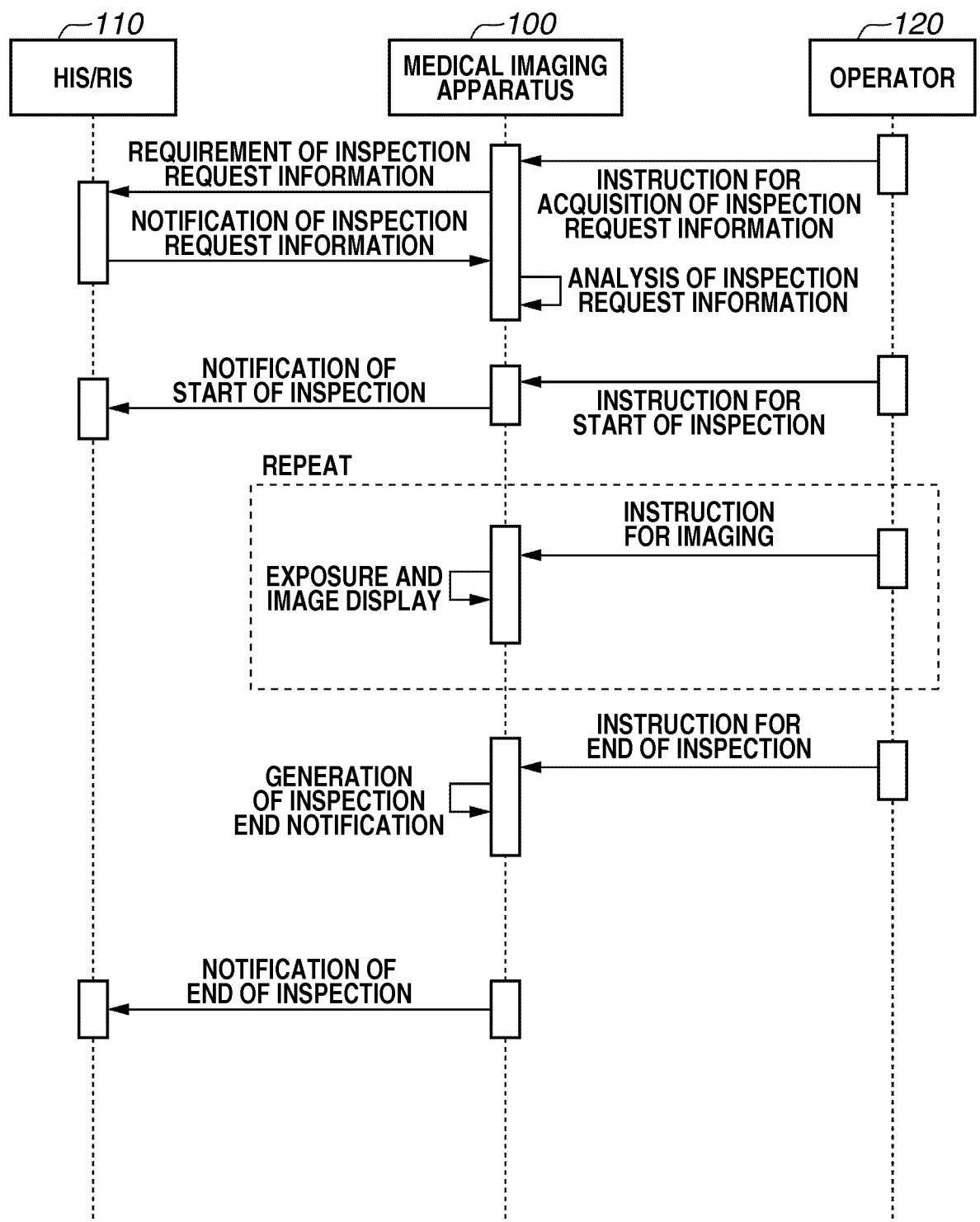

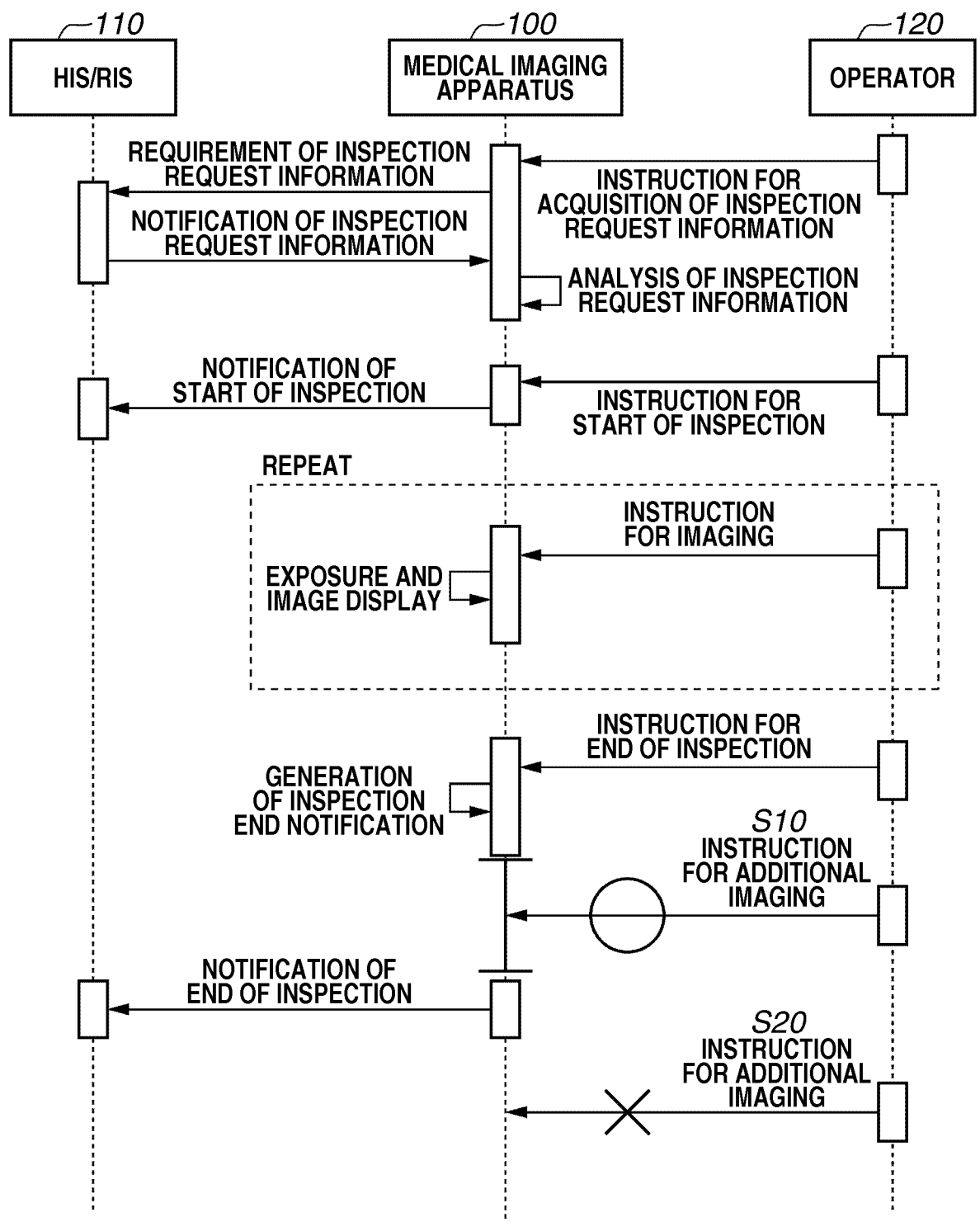

MEDICAL IMAGING APPARATUS, INFORMATION PROCESSING METHOD, AND COMPUTER-READABLE STORAGE MEDIUM

CROSS-REFERENCE TO RELATED APPLICATIONS

This application is a Continuation of U.S. patent application Ser. No. 14/818,110 filed Aug. 4, 2015, which is a continuation of U.S. patent application Ser. No. 14/160,255, now U.S. Pat. No. 9,129,049, filed Jan. 21, 2014, which is a Continuation of application Ser. No. 12/764,003 filed Apr. 20, 2010, now abandoned, which claims foreign priority benefit of Japanese Patent Application No. 2009-106730 filed Apr. 24, 2009. The disclosures of all above-named applications are incorporated by reference herein in their entirety.

FIELD OF THE INVENTION

The present invention relates to a medical imaging apparatus, an information processing method, and a computer-readable storage medium.

BACKGROUND OF THE INVENTION

Medical imaging apparatuses for acquiring a medical image through which a medical doctor checks or diagnoses the medical condition of a patient are known. A medical imaging apparatus can include one or a combination of various types of apparatus such as an X-ray imaging apparatus and an X-ray computed tomography (CT) apparatus using radiation, a magnetic resonance imaging (MRI) apparatus typified by an MRI, and a nuclear medicine imaging apparatus and an ultrasonic imaging apparatus typified by positron emission computerized-tomography (PET) and single photon emission computed tomography (SPECT). The medical images acquired by these medical imaging apparatuses may include various types of images such as a morphological image and one in which a functional value is imaged like a blood flow rate in the brain, for example. A medical doctor determines a required image according to the medical condition of a patient and carries out a diagnosis based on the image acquired by using a medical imaging apparatus accompanied by the determination of the doctor.

In recent years, medical imaging apparatuses can transfer information within an intra-hospital information system via a network to smoothly and accurately conduct an inspection using these medical imaging apparatuses. The intra-hospital information system includes a hospital information system (HIS) for managing information such as patient's information including patient name and patient ID, for example, and inspection request information including inspection date and imaged contents. In particular, the intra-hospital information system includes a radiology information system (RIS) for managing information such as patient's information and inspection request information in the department of radiology. To complement the intra-hospital information system, there exists an image storage and display apparatus whereby an acquired medical image is stored and displayed to be used for diagnosis. Digital Imaging and Communication in Medicine (DICOM) and Health Level Seven (HL7) are stipulated as standards for transmitting information between the intra-hospital information system and a medical imaging apparatus via a network.

The Integrated Healthcare Enterprise (IHE) initiative promotes integration of healthcare information resources to improve clinical care. In IHE, guidelines for promoting integration of the multi-vendors of the intra-hospital information systems have been proposed by unifying the method of using the DICOM and HL7 standards.

The outline of communication between the medical imaging apparatus and HIS/RIS during an inspection request (the issuance of an order) is described with reference to FIG. 22. FIG. 22 illustrates an example of a sequence diagram for transmitting inspection request information between the medical imaging apparatus and HIS/RIS.

As illustrated in FIG. 22, a medical imaging apparatus 100 requests inspection request information to a HIS/RIS 110 according to an instruction to acquire the inspection request information from an operator 120 using a search condition and acquires the inspection request information complying with the search condition. The medical imaging apparatus 100 analyzes the acquired inspection request information. The medical imaging apparatus 100 sends an inspection start notification according to an instruction to start inspection in which the operator 120 selects an inspection to be conducted from the acquired inspection request information. Then, the medical imaging apparatus 100 irradiates an object with X rays, for example, according to an instruction to execute the imaging operation from the operator 120 to acquire a medical image data. This process is repeated as required. The medical imaging apparatus 100 generates an inspection end notification according to an instruction to end the inspection from the operator 120 and notifies the HIS/RIS 110 of the end of the inspection.

In the execution of inspection in the case where a communication is made using the HIS/RIS 110, the medical imaging apparatus 100 notifies the HIS/RIS 110 of the start and end of inspection when the inspection is started or ended (including interruption). Thus, the HIS/RIS 110 can detect a state of execution of the medical imaging apparatus 100 in each inspection to be requested. The timing at which the medical imaging apparatus 100 notifies the HIS/RIS 110 of the start and end of inspection is determined by the operator 120 pressing inspection start or inspection end buttons, respectively, via a graphical user interface (GUI) on the medical imaging apparatus 100. Alternatively, for the notification of the end of inspection, the medical imaging apparatus 100 notifies the HIS/RIS 110 of the end of the previously conducted inspection at the timing at which the next inspection is started. This allows smoothly conducting various processes in the intra-hospital information system.

The information about the end of inspection of which the medical imaging apparatus 100 notifies the HIS/RIS 110 includes information about the number of captured images used for accounting for inspection. For example, if the operator 120 inadvertently leaves the medical imaging apparatus 100 as it is without issuing the instruction to end the inspection thereto, the medical imaging apparatus 100 does not notify the HIS/RIS 110 of the end of inspection. This causes a problem with the workflow such as incorrect or inaccurate accounting after the inspection. As remedies for solving such problems caused by the operator's failure in issuing the "end of inspection" instruction, there is discussed a technique in which ending conditions for ending the inspection are stored in advance into a medical imaging apparatus (refer to Japanese Patent Application Laid-Open No. 2007-215685, for example). Such a medical imaging apparatus automatically ends the inspection to be conducted at the timing at which the ending conditions are satisfied and notifies the HIS/RIS 110 of the end of inspection.

The medical imaging apparatus is capable of communicating with an image storage and display apparatus aside from the HIS/RIS as a imaging flow via a network. The image captured by the medical imaging apparatus is transferred to and stored in the image storage and display apparatus as a dedicated image storage server because the capacity of the medical imaging apparatus alone is insufficient to store the image. Typically, the medical imaging apparatus requests the image storage and display apparatus to store the image data by itself, and the image storage and display apparatus responds at the time when the image storage and display apparatus stores the image data. Such a process can ensure that the image data is properly stored in the image storage and display apparatus. The DICOM protocol stipulates the request for storage as "storage commitment." The medical imaging apparatus may discard the stored image data by receiving the response from the image storage and display apparatus. Since the image storage and display apparatus includes a monitor whose definition is higher than that of a monitor of the medical imaging apparatus, the operator can examine an image with a higher definition by displaying the image data using an image viewer. The timing at which the medical imaging apparatus requests the image storage and display apparatus to store the image data is determined by the operator pressing inspection start or end buttons via the GUI on the medical imaging apparatus as is the case with the aforementioned notification of the end of inspection.

In the execution of inspection in the case where a communication is made using the above HIS/RIS, it is impossible to add a new inspection request to the inspection in which the medical imaging apparatus has once notified the HIS/RIS of the end of the inspection. FIG. 23 illustrates, as described below, that during communication between the medical imaging apparatus and the HIS/RIS, it is impossible to add a new (additional) inspection request.

As indicated in step S10 in FIG. 23, even if the medical imaging apparatus 100 generates an inspection end notification according to the instruction to end the inspection from the operator 120, it is possible to instruct the medical imaging apparatus 100 to add an additional imaging inspection unless the medical imaging apparatus 100 has notified the HIS/RIS 110 of the end of inspection. On the other hand, as indicated in step S20, if additional imaging inspection needs to be added after the medical imaging apparatus 100 has notified the HIS/RIS 110 of the end of inspection, it is impossible to instruct the medical imaging apparatus 100 to add the additional imaging inspection. For this reason, if inspection is conducted again, inspection request information needs to be generated again and an inspection request information notification needs to be received. In this case, however, the inspection needs to be repeated twice. Repetition on inspection represents a problem in that it increases patient burden.

For the medical imaging apparatus conforming to the DICOM standards, there is a method in which an Unscheduled Procedure Step P prepared for an unidentified patient urgently carried to hospital is used to conduct an additional inspection and integrate inspection information thereafter. In this case, it is essential for the medical imaging apparatus to conform to the DICOM standard, and integrating inspection information after inspection is performed may represent a problem in that a risk of inconsistency of data is increased.

On the other hand, as stated above, information about the number of captured images included in the end of inspection notification is used for accounting after inspection. Therefore, in the inspection taking a short time from the end of inspection to accounting such as the inspection for an outpatient, for example, it is required to transmit an end of inspection notification as quickly as possible after the inspection ends. For a group medical examination, for example, it is not required to transmit an end of inspection notification quickly because a plurality of patients takes a medical examination and accounting is collectively performed later in most cases. In other words, the timing at which the transmission of the end of inspection notification is required is different according to the type of inspection in a clinical site.

Complicatedness in inspection is greatly changed with contents to be imaged. The complicatedness in inspection is the greatest factor affecting the operator's mistake and misjudgment. If such a factor is solved by the conventional method of sending the end of inspection notification at the timing an inspection end button is pressed or the next inspection is started, a problem is caused in that the end of inspection end notification is not sent when accounting is requested or notification about the end of inspection desired to be added has been sent. Furthermore, since the end of inspection notification is sent at the same timing regardless of the complicatedness in inspection in all inspections, there is another problem that a follow-up to the operator is not realized on a complicated inspection high in necessity for the addition of inspection.

SUMMARY OF THE INVENTION

According to an aspect of the present invention, a medical imaging apparatus capable of communicating with a hospital information system includes an image data acquisition unit configured to execute an imaging operation to acquire image data based on inspection information, an inspection end information generation unit configured to generate inspection end information indicating a content of the imaging operation executed when the image data is acquired by the image data acquisition unit, a transmission suspension time determination unit configured to determine a transmission suspension time from when the inspection is ended to when the inspection end information generated by the inspection end information generation unit is transmitted to the hospital information system based on inspection information, an inspection end information transmission unit configured to transmit the inspection end information generated by the inspection end information generation unit to the hospital information system after the transmission suspension time determined by the transmission suspension time determination unit has passed after the inspection is ended, and an additional imaging-operation instruction determination unit configured to determine whether an additional imaging operation instruction is issued before the transmission suspension time determined by the transmission suspension time determination unit passes, wherein if the additional imaging-operation instruction determination unit determines that the additional imaging operation instruction is issued, the inspection end information generation unit generates inspection end information including a content of the imaging operation additionally executed according to the additional imaging operation instruction, and the inspection end information transmission unit transmits the inspection end information including the content of the additional imaging operation.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 6 illustrates an example of a correspondence table between an index score total value and the transmission suspension time.

FIG. 22 illustrates a sequence diagram for a medical imaging apparatus and HIS/RIS.

FIG. 23 illustrates a sequence diagram for a medical imaging apparatus and HIS/RIS.

DESCRIPTION OF THE EMBODIMENTS

Various exemplary embodiments, features, and aspects of the invention will be described in detail below with reference to the drawings.

The configuration and operation of a medical imaging apparatus according to a first exemplary embodiment of the present invention is described below.

Figure 1:
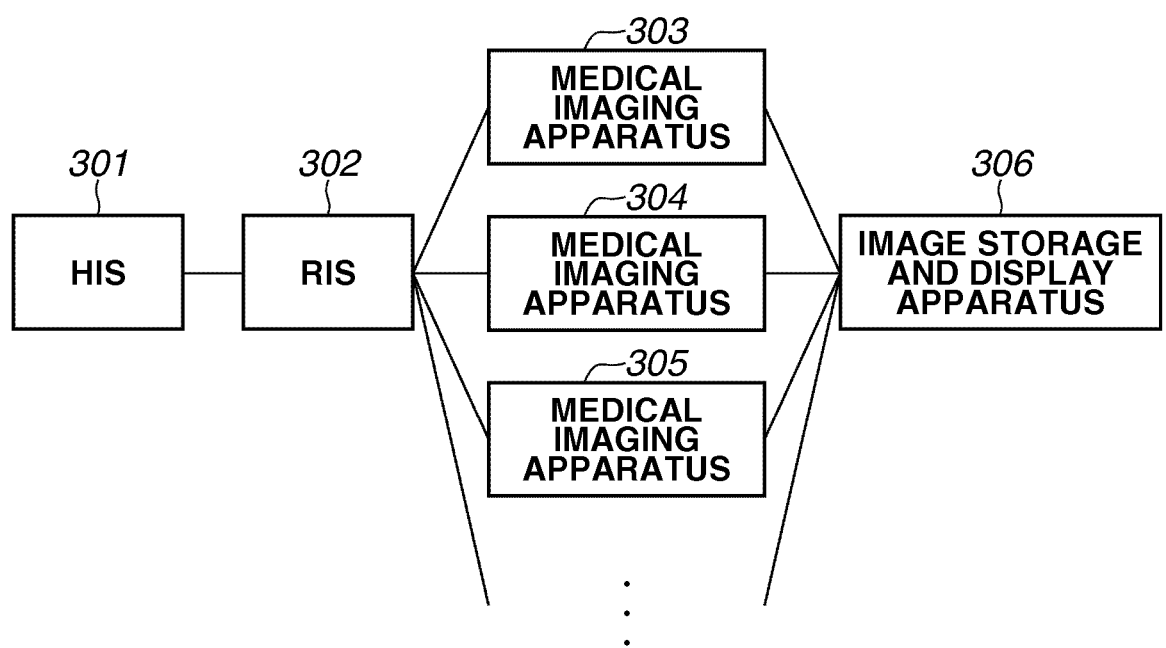
FIG. 1 is a block diagram illustrating an example of an intra-hospital information system capable of communicating with a medical imaging apparatus via a network.

FIG. 1 is a block diagram illustrating an example of an intra-hospital information system capable of communicating with the medical imaging apparatus via a network. As illustrated in FIG. 1, the medical imaging apparatuses 303, 304, and 305 are connected to a HIS 301, a RIS 302, and an image storage and display apparatus 306 as the intra-hospital information system, via one or various networks, such as local area network (LAN) or the like.

Patient information, inspection request information, inspection execution information, inspection end information, image data, and image storage request are transferred using the network. The medical imaging apparatuses 303, 304, and 305 may be of one or plural types. The number of medical imaging apparatuses to be connected is not limited to three apparatus illustrated in FIG. 1 but may be one or more. In the following description, the medical imaging apparatus 303 is described.

The medical imaging apparatus 303 may be any one or a combination of an X-ray imaging apparatus, an X-ray CT apparatus, a magnetic resonance imaging apparatus typified by an MRI, and a nuclear medicine imaging apparatus and an ultrasonic imaging apparatus typified by PET and SPECT, or may include any imaging apparatus for a medical purpose. In the description of the present exemplary embodiment and the other exemplary embodiments described below, the X-ray imaging apparatus is used as an example of the medical imaging apparatus. For the sake of simplicity, in FIG. 1, although a single HIS 301, RIS 302, and image storage and display apparatus 306 are connected to the medical imaging apparatus 303, the number of these apparatuses is not limited to this case. For example, a plurality of HISs 301, RISs 302, and image storage and display apparatus 306 may be connected to the single medical imaging apparatus 303.

Patient information, inspection request information, inspection execution information, and inspection end information used in the present exemplary embodiment are described below. In the present exemplary embodiment, four types of the information can be collectively referred to as inspection information.

The patient information refers to individual information of a patient being a subject inspected by the medical imaging apparatus 303. The patient information includes a patient ID that is a unique ID for identifying a subject, a patient name, sex, date of birth, and age. The patient information is input and stored mainly by the HIS 301. The RIS 302 and the medical imaging apparatus 303 can also input and store the patient information. The patient information is stored in an information storage apparatus such as a server connected to a network to allow sharing patient information input by each apparatus with the consistency of the patient information ensured.

The inspection request information refers to a specific inspection execution request in which when an inspection conducted by the medical imaging apparatus 303 is performed using which medical imaging apparatus by who and what kind of image is taken. The inspection request information mainly includes information about an inspection ID that uniquely identifies an inspection, inspection execution schedule date, inspection execution schedule apparatus, and specific imaging techniques executed at the inspection. There is also included the name of an engineer (hereinafter referred to as an operator) who conducts inspection, names of a department and a doctor who request the inspection and the above patient information. If the HIS 301, the RIS 302, and the medical imaging apparatus 303 conform to the DICOM standards, the inspection request information includes tag information stipulated by MODALITY WORK LIST SOP class (hereinafter referred to as MWL) of the DICOM standards. The inspection request information is input and stored mainly by the HIS 301. The RIS 302 and the medical imaging apparatus 303 can also input and store the inspection request information. In this case, the HIS 301 is notified of the inspection request information at any timing. The inspection request information is stored an information storage apparatus such as a server connected to the network to allow sharing the inspection request information between the apparatus.

The inspection execution information refers to information as to a specific imaging operation executed at the ended inspection. The inspection execution information includes information about executed imaging techniques, the number of captured images, time required for execution the inspection, the presence or absence of addition of imaging during the inspection, the name of an operator execution the inspection, the total amount of radiation dose to which a patient is exposed during the inspection. The executed imaging techniques include information about the name of imaging techniques, an imaged region (including left and right), imaging direction and attitude of a patient in each imaging technique, still imaging in each imaging technique, and imaging methods of moving image and angiography. The inspection execution information is generated and used only by the medical imaging apparatus 303.

The inspection end information refers to information indicating actually executed contents in the inspection request information which the operator selects by the medical imaging apparatus 303. The inspection end information mainly includes information about an inspection ID that uniquely identifies the inspection, inspection execution date, a medical imaging apparatus whereby the inspection is conducted, and the name of an operator conducting the inspection. The inspection end information also includes the above patient information and inspection execution information. If the HIS 301, the RIS 302, and the medical imaging apparatus 303 conform to the DICOM standards, the inspection end information includes tag information stipulated by Modality Performed Procedure Step Stop class (PPS) of the DICOM standards. The inspection end information is generated when the medical imaging apparatus 303 ends the inspection. Thereafter, the medical imaging apparatus 303 transmits the inspection end information to the RIS 302 at the timing set for each inspection. After that, the RIS 302 transmits the inspection end information to the HIS 301. The inspection end information is used in the work flow such as accounting after the inspection.

Each apparatus illustrated in FIG. 1 is described below.

The HIS 301 transfers information with the RIS 203 via the network. The HIS 301 being one of the intra-hospital information systems, registers the patient information, generates the inspection request information and transmits the generated patient information and inspection request information to the RIS 302. The HIS 301 receives an inspection start notification and an inspection end notification from the medical imaging apparatus 303 via the RIS 302. On receipt of the inspection end notification, the HIS 301 performs hospital information processing using inspection end information attached to the inspection end notification.

The RIS 301 being one of the intra-hospital information systems concerning the department of radiology in a hospital is connected to the HIS 301 and the medical imaging apparatus 303 via the network. The RIS 302 receives the inspection request information from the HIS 301 and transmits the received inspection request information to the medical imaging apparatus 303. The RIS 302 receives the inspection start notification and the inspection end notification from the medical imaging apparatus 303 and transmits the received inspection start notification and inspection end notification to the HIS 301.

The medical imaging apparatus 303 is connected to the RIS 302 and the image storage and display apparatus 306 via the network. The medical imaging apparatus 303 receives the inspection request information from the RIS 302 and stores the received inspection request information therein. When the inspection is executed, the medical imaging apparatus 303 displays the received inspection request information on a monitor of the medical imaging apparatus 303 using a user interface (GUI) and executes the inspection selected by the operator. The medical imaging apparatus 303 transmits the inspection start notification and inspection end notification to the RIS 302.

The medical imaging apparatus 303 transmits medical image data (hereinafter referred to as image data) acquired by imaging at the inspection to the image storage and display apparatus 306 if required. The medical imaging apparatus 303 transmits an image storage request as well as the image data to the image storage and display apparatus 306. The image storage request refers to notification information which requests the image storage and display apparatus 306 to store the image data stored in the medical imaging apparatus 303 at the time of ending the inspection.

The image storage and display apparatus 306 is an image server which receives the image data transmitted from the medical imaging apparatus 303 and stores the image data therein. When the image storage and display apparatus 306 receives the image storage request, the image storage and display apparatus 306 stores the received image data therein in a similar manner or stores the received image data in an external recording medium as the case may be. When the image storage and display apparatus 306 ends storage processing, the image storage and display apparatus 306 transmits response to the medical imaging apparatus 303. The image storage and display apparatus 306 functions as a medical image viewer for receiving the image data transmitted from the medical imaging apparatus and displaying the image data.

When the medical imaging apparatus 303 receives a response from the image storage and display apparatus 306, the medical imaging apparatus 303 can confirm that the storage of the image data into another recording medium is ended, so that the medical imaging apparatus 303 can freely manage the image data stored therein.

Figure 2:
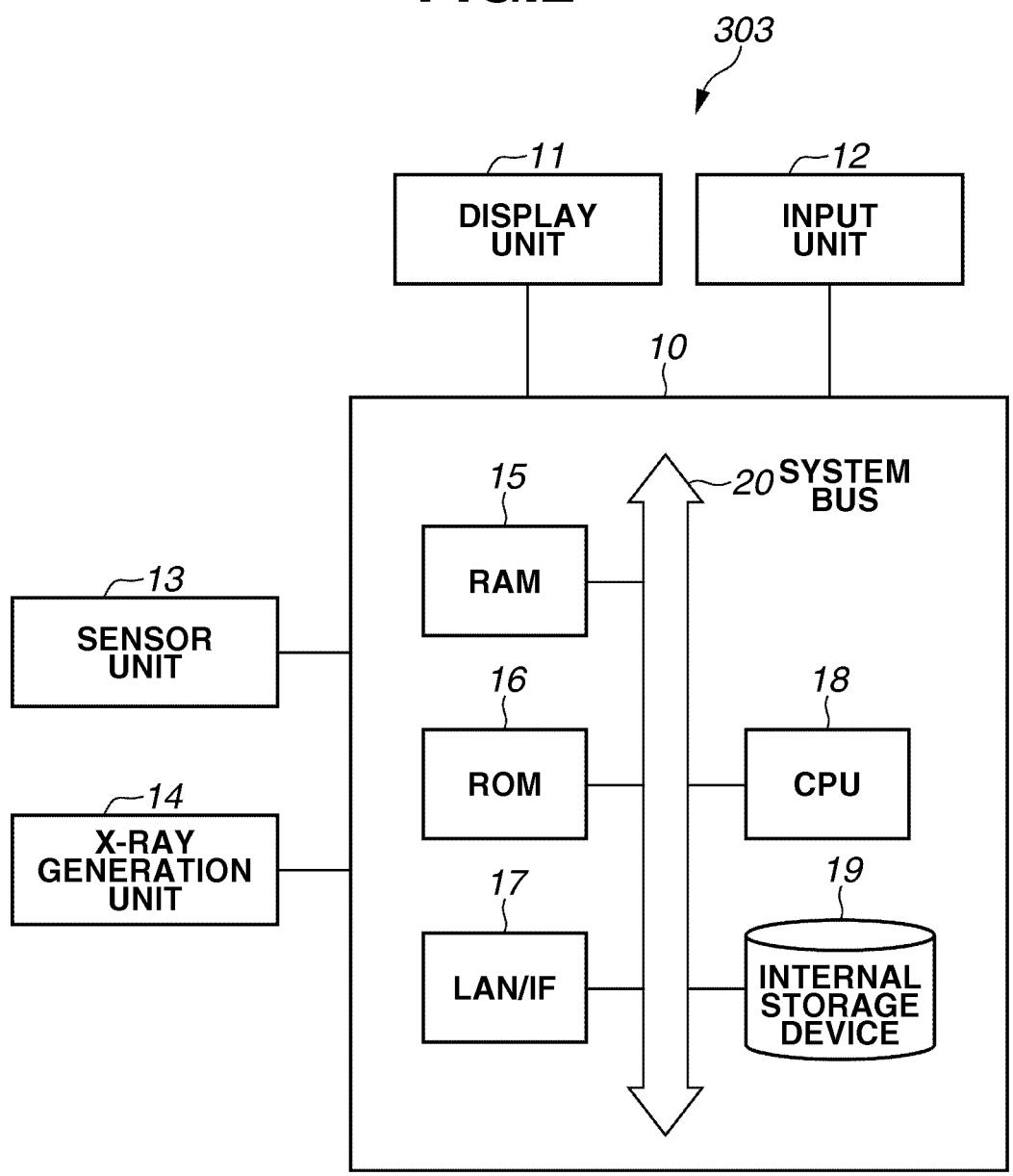
FIG. 2 is a block diagram illustrating an example of hardware configuration of the medical imaging apparatus.

An example of the hardware configuration of the medical imaging apparatus according to the present exemplary embodiment is described below with reference to FIG. 2. As illustrated in FIG. 2, the medical imaging apparatus 303 includes an information processing unit 10, a display unit 11, an input unit 12, a sensor unit 13, an X-ray generation unit 14. The information processing unit 10 is configured such that a RAM 15, a ROM 16, a LAN/IF 17, a CPU 18, and an internal storage device 19 such as a hard disk are connected to one another via a system bus 20. Thus, the information processing unit 10 includes a general computer configuration. The display unit 11 includes a general monitor such as a liquid crystal display. The display unit 11 displays the image data and a graphical user interface (GUI) on a screen. The input unit 12 includes an input apparatus such as a mouse, a keyboard, a bar code reader, or the like. The operator can input various commands and data into the information processing unit 10 using the input unit 12. The X-ray generation unit 14 irradiates a patient with X-rays. The sensor unit 13 receives the X-rays transmitted through the patient and generates image data.

Figure 3:
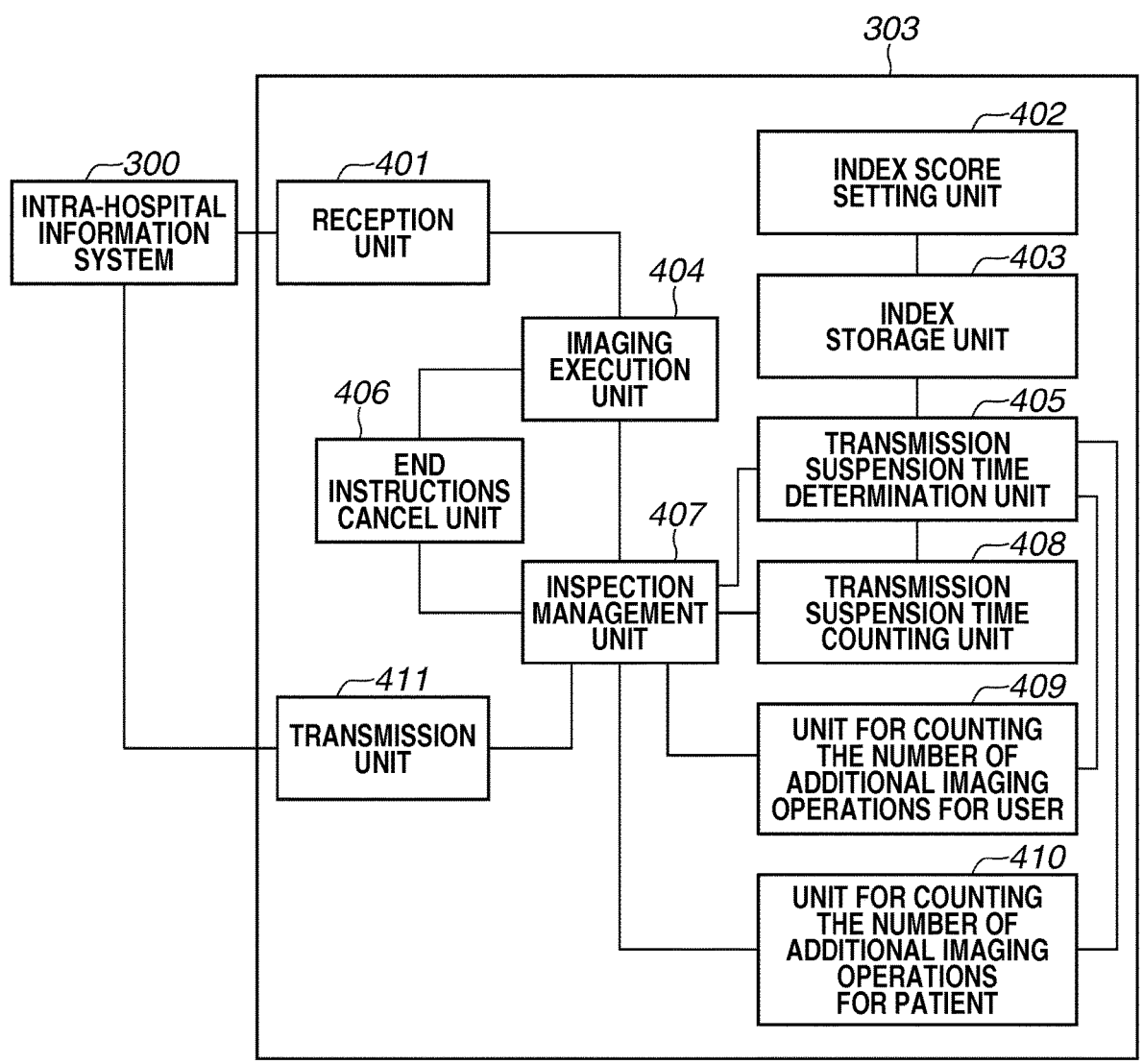
FIG. 3 is a block diagram illustrating an example of functional configuration of the medical imaging apparatus according to the first exemplary embodiment of the present invention.

An example of the functional configuration of the medical imaging apparatus according to the present exemplary embodiment is described below with reference to FIG. 3. FIG. 3 illustrates an example of the functional configuration of the medical imaging apparatus. The functional configuration of the medical imaging apparatus illustrated in FIG. 3 is implemented by the CPU 18 executing the programs stored in the ROM 16 and the internal storage device 19. In FIG. 3, the HIS 301, the RIS 302, and the image storage and display apparatus 306 illustrated in FIG. 1 are consolidated into an intra-hospital information system 300.

A reception unit 401 communicates with the intra-hospital information system 300 and in particular receives the inspection request information.

An imaging execution unit 404 stores the inspection request information received by the reception unit 401, displays the list thereof, and executes an imaging operation according to the instruction of the operator. The imaging execution unit 404 transmits the inspection request information to an inspection management unit 407 along with the start of the inspection and transmits the inspection execution information and the acquired image data to the inspection management unit 407 along with the end of the inspection.

The inspection management unit 407 controls the GUI displayed on the display unit 11 of the medical imaging apparatus 303 according to the operation of the operator via the input unit 12. The inspection management unit 407 manages the state of the inspection on all inspection information stored in the medical imaging apparatus 303 and generates the inspection end information attached to the inspection end notification for the intra-hospital information system 300.

A transmission unit 411 communicates with the intra-hospital information system 300 to transmit the inspection end notification and image data.

A transmission suspension time determination unit 405 receives the inspection request information, patient information, inspection execution information, information about the number of additional imaging operations for operator, and information about the number of additional imaging operations for patient to calculate an index score by referring to an index storage unit 403, determining a transmission suspension time for each inspection.

A transmission suspension time counting unit 408 receives an instruction to start counting from the transmission suspension time determination unit 405 and starts counting. The transmission suspension time counting unit 408 counts a transmission suspension time and then transmits a counting end notification to the inspection management unit 407.

A "unit for counting the number of additional imaging operations for user" 409 counts the number of additional imaging operations for each operator using user information stored inside each time the "unit for counting the number of additional imaging operations for user" 409 is notified of the additional imaging operation by the inspection management unit 407.

A "unit for counting the number of additional imaging operations for patient" 410 counts the number of additional imaging operations for each patient using patient information stored inside each time the "unit for counting the number of additional imaging operations for patient" 410 is notified of the additional imaging operation by the inspection management unit 407.

The index storage unit 403 stores: each item included in the inspection request information, patient information, inspection execution information, information about the number of additional imaging operations for user, and information about the number of additional imaging operations for patient; index scores set thereto; and a weighting coefficient for each item. The index storage unit 403 includes the internal storage device 19 and a program for controlling the internal storage device 19. In the present exemplary embodiment, although the index storage unit 403 is included in the medical imaging apparatus 303, in another alternative, the index storage unit 403 may be directly connected to the medical imaging apparatus 303 from the outside using a connection interface such as USB, for example. The index storage unit 403 may be comprised of an information storage server to be connected to a plurality of the medical imaging apparatus 303 via the network. The plurality of the medical imaging apparatus 303 shares the index storage unit 403 therebetween via the network to eliminate the need for setting the index scores in each medical imaging apparatus 303, facilitating the management of index scores, which enables the improvement of consistency between the index scores.

An index score setting unit 402 determines whether each item stored in the index storage unit 403 is used as an index score. If each item is used, the index score setting unit 402 changes the score and the value of weighting coefficient for each item.

An end instruction cancel unit 406 shifts a state where an inspection is ended and a transmission is suspended to a state where the inspection is being executed again.

Figure 4:
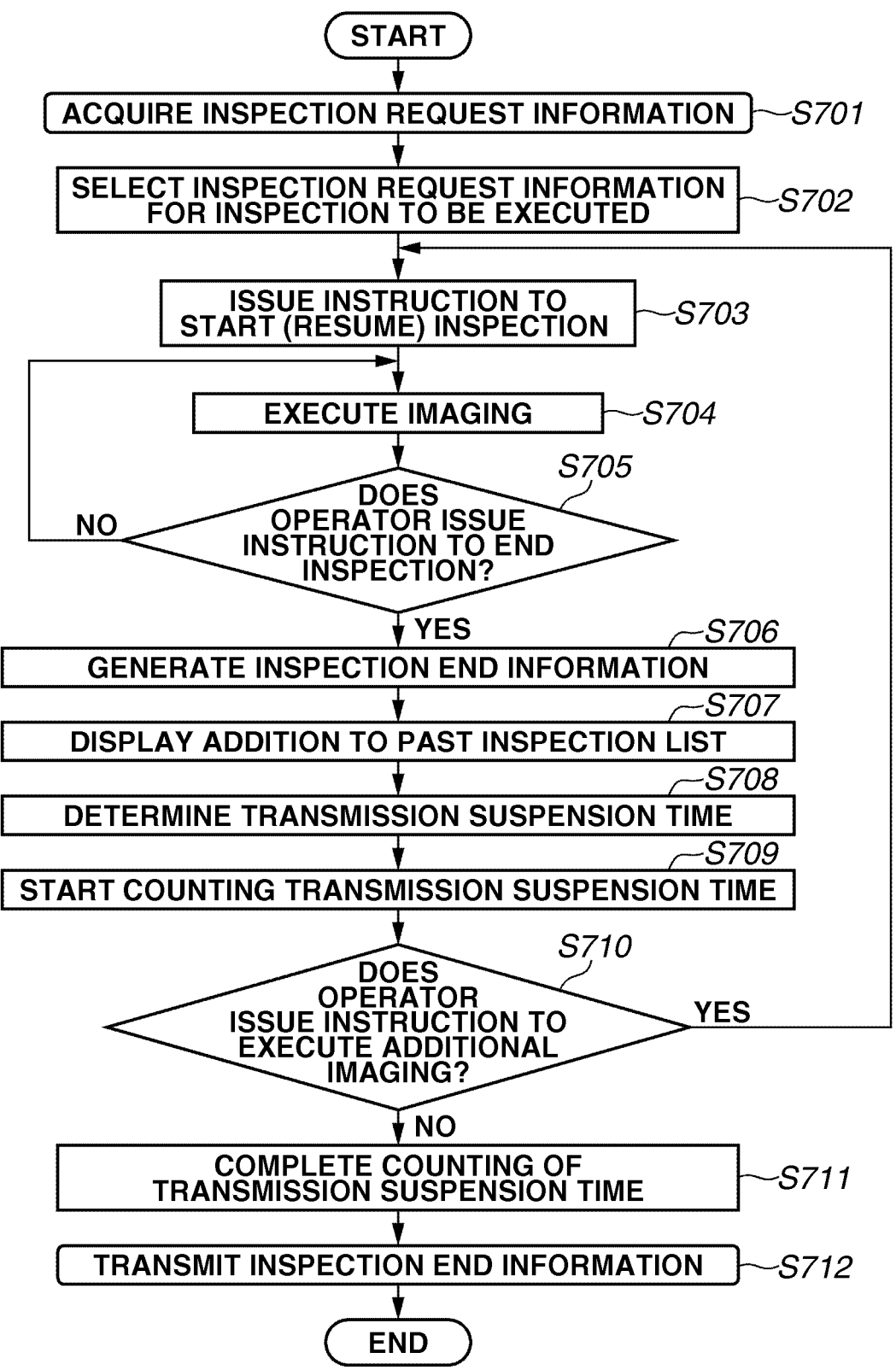
FIG. 4 is a flow chart illustrating an example of the operation processing of the medical imaging apparatus according to the first exemplary embodiment.

The operation processing of the medical imaging apparatus according to the present exemplary embodiment is described below with reference to the flow chart illustrated in FIG. 4. FIG. 4 is a flow chart illustrating an example of the operation processing performed from the time of reception of the inspection request information to the time of transmission of the inspection end notification. The processing is implemented by the CPU 18 of the medical imaging apparatus 303 executing the program stored in the ROM 16.

In step S701, the transmission unit 411 requests the intra-hospital information system 300 to transmit the inspection request information via the network. The request is made when the operator mainly presses the acquisition instruction button for the inspection request information displayed on the GUI of the display unit 11 of the medical imaging apparatus 303. Alternatively, the transmission unit 411 may automatically make a request every predetermined time interval or may make a request at the timing at which the operator issues an instruction to display the inspection request information as a list. The timing is not limited only to the above.

When the transmission of the inspection request information is required, an acquisition condition can be set to an item included in the inspection request information. In other words, the transmission unit 411 requires the intra-hospital information system 300 with at least one acquisition condition input. In this case, the intra-hospital information system 300 extracts the inspection request information in which an inspection is not yet started and which matches with the acquisition condition from the stored inspection request information and transmits the inspection request information to the medical imaging apparatus 303. If the acquisition condition is not set, the intra-hospital information system 300 transmits all pieces of the inspection request information in which an inspection is not yet started among the inspection request information stored at present. The reception unit 401 of the medical imaging apparatus 303 receives the transmitted inspection request information. The reception unit 401 then transmits the acquired inspection request information to the imaging execution unit 404. The imaging execution unit 404 lists the received inspection request information to display the list on the display unit 11 with the GUI and stores the inspection request information in the internal storage device 19.

In step S702, the operator selects the inspection request information to be executed from the inspection request information displayed as the list. The imaging execution unit 404 switches the inspection request information selected by the operator to detailed information and displays the detailed information.

In step S703, the operator presses the inspection start button displayed by the GUI on the display unit 11.

In step S704, the imaging execution unit 404 starts inspection based on the inspection request information selected according to the operator's instruction to start the inspection. At this point, the imaging execution unit 404 instructs the transmission unit 411 via the inspection management unit 407 to send the inspection start notification to the intra-hospital information system 300. The transmission unit 411 transmits the inspection start notification to the intra-hospital information system 300. After that, the imaging execution unit 404 repetitively executes imaging operations according to the operator's instruction to execute the imaging operations to acquire image data.

In step S705, the imaging execution unit 404 determines whether the operator issues an instruction to end the inspection. The operator presses the inspection end button displayed by the GUI on the display unit 11 when the operator ends all the imaging operations and the post processing required for the inspection. If the imaging execution unit 404 receives the operator's instruction to end the inspection (YES in step S705), the imaging execution unit 404 advances the processing to step S706. If the imaging execution unit 404 does not receive the operator's instruction to end the inspection (NO in step S705), the imaging execution unit 404 returns the processing to step S704.

In step S706, the imaging execution unit 404 ends the inspection which is being executed and generates the inspection execution information based on the inspection execution result. Thereafter, the imaging execution unit 404 transmits the inspection request information, the generated inspection execution information, and the acquired image data to the inspection management unit 407. The inspection management unit 407 receives the inspection request information, the inspection execution information, and the image data and shifts an inspection state from the state where the inspection is being executed to the state where a transmission is suspended. The inspection management unit 407 generates the inspection end information which is attached to the inspection end notification to be transmitted to the intra-hospital information system 300 using the inspection request information and the patient information included in the inspection execution information and the inspection request information.

In step S707, the inspection management unit 407 adds a part of the generated inspection end information to a past inspection information list displayed by the GUI on the display unit 11 and displays the list. An example of the GUI that displays an inspection being in the state where a transmission is suspended on the past inspection information list is described below with reference to FIG. 7.

In step S708, the inspection management unit 407 transmits the inspection request information and the inspection execution information to the transmission suspension time determination unit 405. The inspection management unit 407 instructs the "unit for counting the number of additional imaging operations for user" 409 and the "unit for counting the number of additional imaging operations for patient" 410 to transmit the number of additional imaging operations. The "unit for counting the number of additional imaging operations for user" 409 and the "unit for counting the number of additional imaging operations for patient" 410 receive the instruction to transmit the number of additional imaging operations and then transmit the information about the number of additional imaging operations stored therein to the transmission suspension time determination unit 405. The transmission suspension time determination unit 405 receives the inspection request information, the inspection execution information, information about the number of additional imaging operations for user, and information about the number of additional imaging operations for patient. The transmission suspension time determination unit 405 determines a transmission suspension time using a method of determining a transmission suspension time described below.

In step S709, the transmission suspension time determination unit 405 transmits an instruction to start counting to the transmission suspension time counting unit 408. The transmission suspension time counting unit 408 receives the instruction to start counting and then starts counting. The transmission suspension time counting unit 408 ends counting and then transmits the counting end notification to the inspection management unit 407.

In step S710, the imaging execution unit 404 determines whether the operator issues an instruction to execute an additional imaging operation while the transmission suspension time counting unit 408 is counting a transmission suspension time, i.e., before the inspection management unit 407 receives the counting end notification of the transmission suspension time. If the operator does not issue the instruction to execute the additional imaging operation (NO in step S710), the imaging execution unit 404 advances the processing to step S711.

In step S711, the transmission suspension time counting unit 408 transmits the counting end notification to the inspection management unit 407.

In step S712, the inspection management unit 407 shifts the inspection state from the state where a transmission is suspended to the state where the inspection is ended. For the inspection shifted to an end state, the inspection management unit 407 instructs the transmission unit 411 to transmit the inspection end notification, the inspection end information, and the image data. The transmission unit 411 transmits the inspection end notification, to which the inspection end information is added, and the image data to the intra-hospital information system 300 corresponding thereto.

The inspection management unit 407 updates the past inspection information list displayed by the GUI on the display unit 11. More specifically, the inspection management unit 407 changes indication in the column of "inspection end information notification" of the inspection being in the end state on the past inspection list to "Ended." An example of the GUI for updating the past inspection list is described below in FIG. 7.

The intra-hospital information system 300 receives the inspection end notification, to which the inspection end information is added, and the image data. Then, the image storage and display apparatus 306 stores the received image data and the RIS 302 manages the inspection end information in a database.

On the other hand, if the imaging execution unit 404 determines that the operator instructs the execution of the additional imaging operation (YES in step S710), the imaging execution unit 404 conducts processing for an additional imaging operation described below and the processing returns to step S703. The flow of the inspection after resumption is similar to that in steps S703 to S709 described above.

In other words, if the processing is advanced to step S706 after the inspection is resumed based on the instruction to execute the additional imaging operation, the inspection management unit 407 updates and generates the inspection end information using the inspection execution information including the imaging operation added by the instruction to execute the additional imaging operation. The inspection management unit 407 may generate new inspection end information using the inspection execution information including the imaging operation added by the instruction to execute the additional imaging operation.

In step S708, the transmission suspension time determination unit 405 determines a transmission suspension time based on the inspection execution information including the imaging operation added by the instruction to execute the additional imaging operation.

In step S712, the transmission unit 411 transmits the inspection end notification to which the updated inspection end information is added and the image data to the intra-hospital information system 300 after the newly determined transmission suspension time passes. If the new inspection end information is generated based on the imaging operation added by the instruction to execute the additional imaging operation, the transmission unit 411 transmits the inspection end information generated before the imaging operation is added and the inspection end information generated after the imaging operation is added.

The resumption of the inspection according to the instruction to execute the additional imaging operation may be repeated over and over again until the counting of the transmission suspension time is ended. Thus, in the present exemplary embodiment, an inspection may be added even to the inspection which is instructed to end unless the transmission suspension time passes, which eliminates the need for inspecting again as a new inspection or consolidating an inspection conducted for an unidentified patient.

Figure 5:
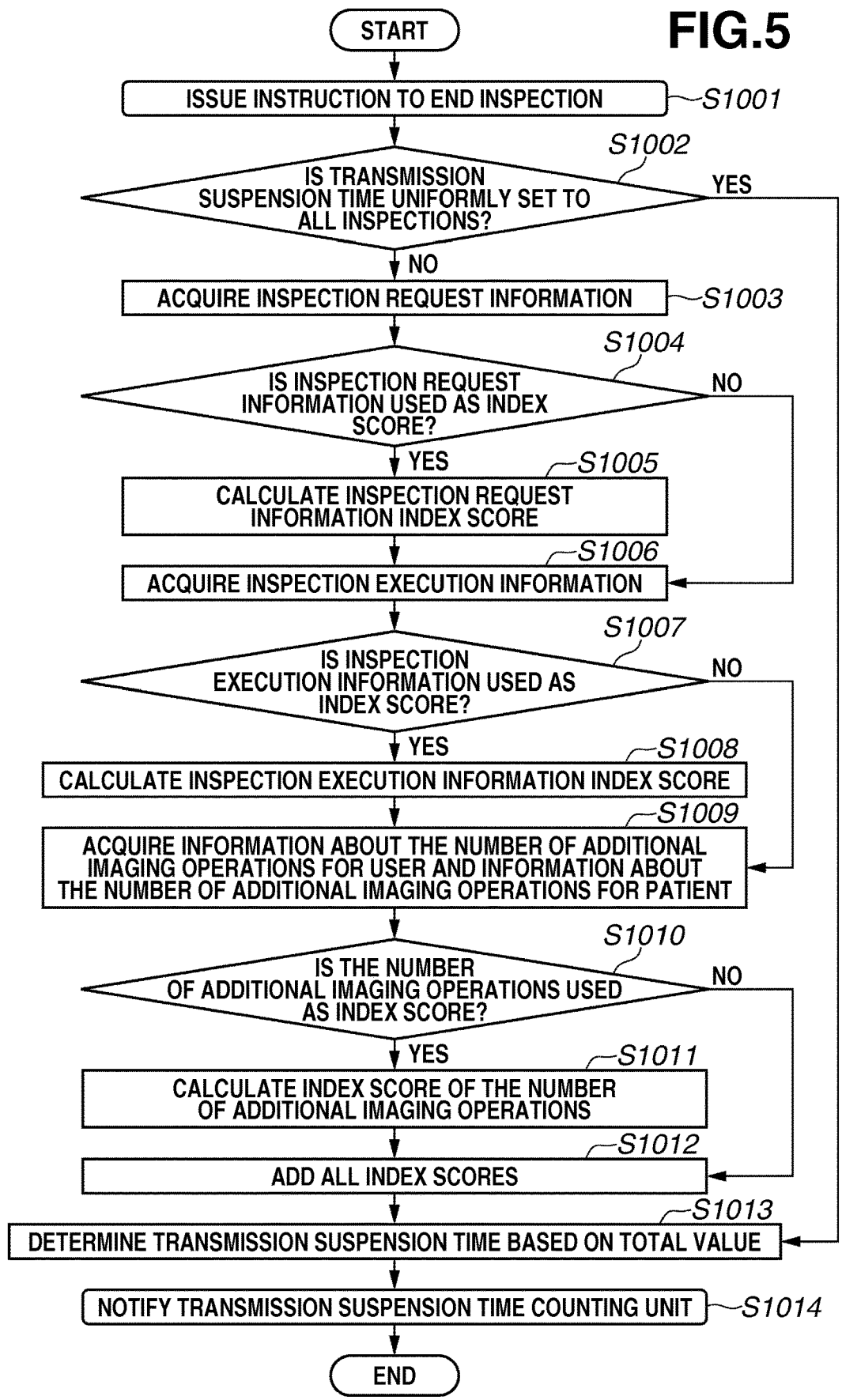
FIG. 5 is a flow chart illustrating an example of operation processing for determining a transmission suspension time.

The operation processing for determining the transmission suspension time in the medical imaging apparatus is described below with reference to a flow chart illustrated in FIG. 5. FIG. 5 is a flow chart illustrating an example of the operation processing performed from the time of issue of the instruction to end the inspection to the time of determination of the transmission suspension time. The processing is implemented by the CPU 18 of the medical imaging apparatus 303 executing the program stored in the ROM 16.

In step S1001, the imaging execution unit 404 determines whether the operator issues an instruction to end the inspection. The processing corresponds to the processing in steps S705 to S706 illustrated in FIG. 4. The inspection management unit 407 transmits the inspection request information and the inspection execution information to the transmission suspension time determination unit 405.

In step S1002, the transmission suspension time determination unit 405 determines whether a transmission suspension time is uniformly set to all inspections irrespective of the inspection information by referring to the index storage unit 403. If the transmission suspension time is uniformly set to all inspections (YES in step S1002), the processing proceeds to step s1013. If the transmission suspension time is not uniformly set to all inspections (NO in step S1002), the processing proceeds to step S1003.

In step S1003, the transmission suspension time determination unit 405 acquires the inspection request information among the information transmitted from the inspection management unit 407.

In step S1004, the transmission suspension time determination unit 405 determines whether the inspection request information is used as an index score by referring to the index storage unit 403. If the inspection request information is not used as an index score (NO in step S1004), the processing proceeds to step S1006. If the inspection request information is used as an index score (YES in step S1004), the processing proceeds to step S1005.

In step S1005, the transmission suspension time determination unit 405 calculates an inspection request information index score based on the acquired inspection request information and the index storage unit 403. More specifically, the transmission suspension time determination unit 405 confirms setting as to whether each item included in the inspection request information is used as an index. In the case of the setting where each item is not used as an index, the transmission suspension time determination unit 405 sets the index score X for the item to 0 and acquires a weighting coefficient A. On the other hand, in the case of the setting where each item is used as an index, the transmission suspension time determination unit 405 acquires the index score X set to the item and the weighting coefficient A. The transmission suspension time determination unit 405 calculates the product of the index score and the weighting coefficient for each item in both cases.

The transmission suspension time determination unit 405 performs the calculation of all items included in the inspection request information (the number of items is assumed to be I) and calculates the total "S SCHEDULED" of the values calculated from all items of the inspection request information.

In step S1006, the transmission suspension time determination unit 405 acquires the inspection execution information among the information transmitted from the inspection management unit 407.

In step S1007, the transmission suspension time determination unit 405 determines whether the inspection execution information is used as an index score by referring to the index storage unit 403. If the inspection execution information is not used as an index score (NO in step S1007), the processing proceeds to step S1009. If the inspection execution information is used as an index score (YES in step S1007), the processing proceeds to step S1008.

In step S1008, the transmission suspension time determination unit 405 calculates an inspection execution information index score based on the acquired inspection execution information and the index storage unit 403. Specifically the processing is similar to that in step S1005, so that the description thereof is omitted. The transmission suspension time determination unit 405 calculates the total "S PERFORMED" of the values calculated from all items of the inspection request information.

In step S1009, the transmission suspension time determination unit 405 acquires information about the number of additional imaging operations for user from the "unit for counting the number of additional imaging operations for user" 409 and acquires information about the number of additional imaging operations for patient from the "unit for counting the number of additional imaging operations for patient" 410.

In step S1010, the transmission suspension time determination unit 405 determines whether the number of additional imaging operations for user or the number of additional imaging operations for patient is used as an index score by referring to the index storage unit 403. If the number of additional imaging operations for user or the number of additional imaging operations for patient is not used as an index score (NO in step S1010), the processing proceeds to step S1012. If the number of additional imaging operations for user or the number of additional imaging operations for patient is used as an index score (YES in step S1010), the processing proceeds to step S1011.

In step S1011, the transmission suspension time determination unit 405 calculates an index score of the number of additional imaging operations based on the acquired number of additional imaging operations for patient and number of additional imaging operations for patient and the index storage unit 403. Specifically the processing is similar to that in step S1005, so that the description thereof is omitted. The transmission suspension time determination unit 405 calculates the total "S ADDEXP" of the values calculated from all items of the number of additional imaging operations for patient and the number of additional imaging operations for patient.

In step S1012, transmission suspension time determination unit 405 calculates the index score total S by adding values "S SCHEDULED," "S PERFORMED" and "S ADDEXP" calculated in the above steps. In this case, the number of additional imaging operations for user or the number of additional imaging operations for patient is not used as an index score, so that zero is substituted for the total in which calculation is omitted.

In step S1013, the transmission suspension time determination unit 405 determines a transmission suspension time from a table of correspondence between the index score total and the transmission suspension time stored in the index storage unit 403.

In 51014, the transmission suspension time determination unit 405 notifies the transmission suspension time counting unit 408 of an instruction to start counting immediately after determining a transmission suspension time. On the other hand, in step S1002, if the transmission suspension time is uniformly set to all inspections, then in step S1013, the transmission suspension time determination unit 405 determines the set suspension time as a transmission suspension time. Consequently, the operator does not need to confirm a transmission suspension time. This offers an advantage of reducing the redundancy of a workflow in which the operator needs to confirm a transmission suspension time because the transmission suspension time of the inspection is unclear when an additional imaging is required, for example.

FIG. 6 illustrates an example of a correspondence table between the index score total value and the transmission suspension time. The information of a correspondence table 1301 illustrated in FIG. 6 is stored in the index storage unit 403. The correspondence table 1301 stores the transmission suspension time of each region of an index score total value. The index score setting unit 402 can previously change the region of an index score total value and the corresponding transmission suspension time in the correspondence table 1301 before the start of the inspection according to the setting of the operator.

Thus, the aforementioned method of determining the transmission suspension time is used to determine the transmission suspension time based on information such as the inspection request information, the inspection execution information and the number of additional imaging operations, allowing the calculation of the transmission suspension time corresponding to inspection. The patient information is included in the inspection request information and not directly used as an index. A patient is identified by patient information to enable identifying the state of a patient to be inspected such as an outpatient and an inpatient and an inspection type (such as a group medical examination, a general medical examination, and a trauma examination, for example). Thus, the inspection is comprehensively determined from various points of view to allow the determination of the transmission suspension time that maintains the balance between information about whether the inspection end notification of the inspection needs to be urgently transmitted and the complicatedness in the inspection. More specifically, for example, patient state information and inspection type information are included in the patient information, thereby the transmission suspension time determination unit 405 determines the transmission suspension time based on the patient state information and the inspection type information included in the patient information.

Figure 7:
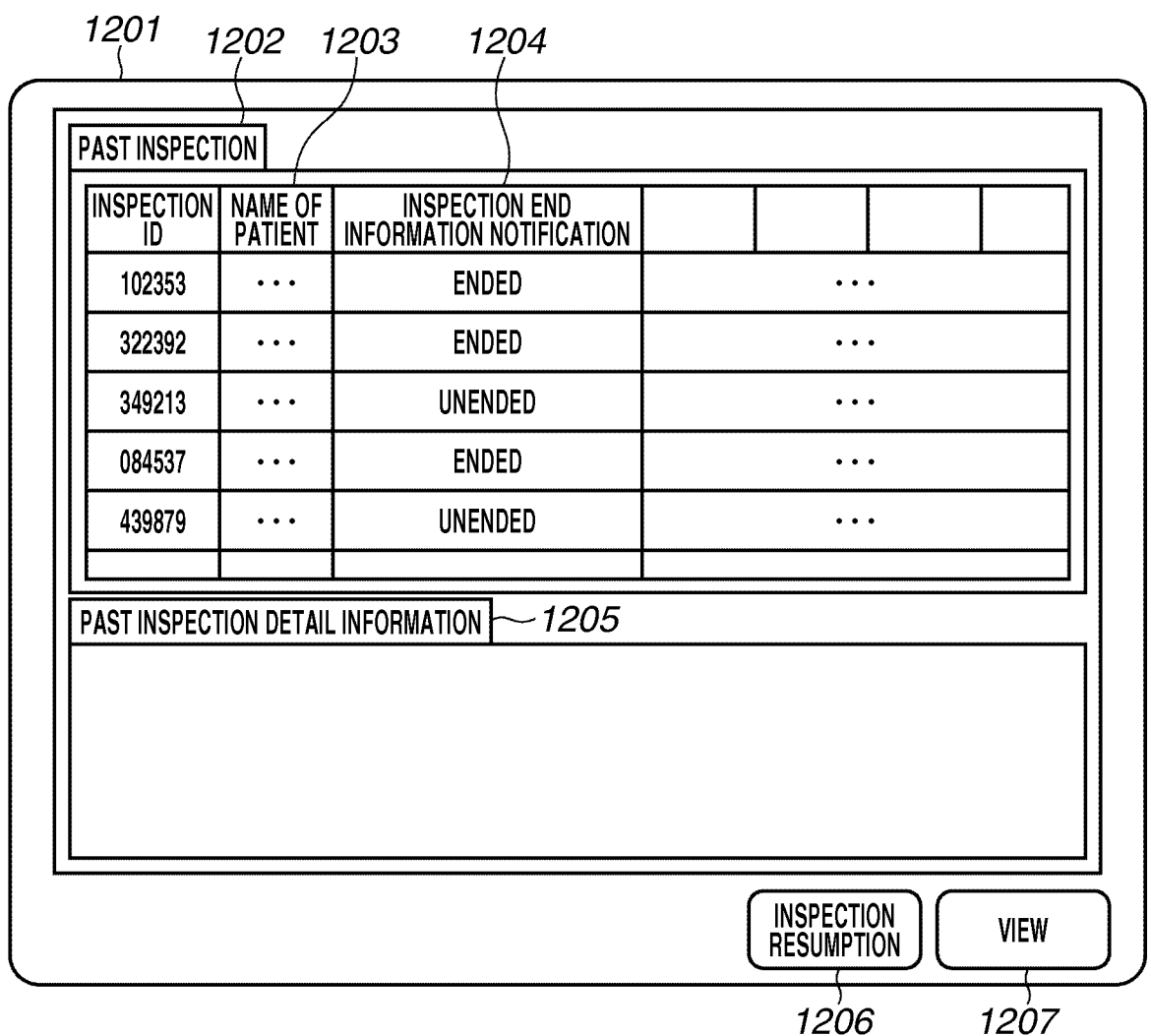
FIG. 7 illustrates an example of a display screen for a past inspection list.

The GUI of the past inspection information list is described below with reference to FIG. 7. FIG. 7 is a chart illustrating an example of a past inspection display screen of the past inspection list displayed in step S707 illustrated in FIG. 4.

A past inspection display screen 1201 illustrated in FIG. 7 indicates a past inspection information list display area 1202. The past inspection information list display area 1202 indicates inspection information both in a transmission suspension state and in an end state. The uppermost row of the past inspection information list display area 1202 is an information item-name indication section 1203 for indicating each item name of the past inspection information. The information item-name indication section 1203 indicates all items included in the inspection end information. Items to be indicated can be selected when the operator changes the setting. If items to be indicated are too many to be listed on the past inspection display screen 1201, the operator may manipulate a scroll bar to confirm all items to be indicated, for example.

The information item-name indication section 1203 includes an inspection end information notification indication section 1204. The inspection end information notification indication section 1204 indicates whether the past inspection indicated in the past inspection information list display area 1202 is in a transmission suspension state or in an end state. The inspection end information notification indication section 1204 in the example of the past inspection display screen 1201 illustrated in FIG. 7 indicates the transmission suspension state with "Unended" and the end state with "Ended." However, this does not hold true provided that the operator identifies the inspection state.

The past inspection display screen 1201 indicates a past inspection detail indication section 1205. The past inspection detail indication section 1205 indicates a detailed summary of the inspection end information about the inspection selected on the past inspection information list display area 1202.

Thus, the operator can refer to the detailed summary of information about the selected inspection on the past inspection detail indication section 1205 by selecting inspection contents indicated on the past inspection information list display area 1202. Incidentally, the operator can confirm neither more specific information about the inspection (for example, image processing parameters used for imaging operations in the inspection) nor the acquired image data via the past inspection display screen 1201. In that case, the operator selects the inspection in which the operator wants to confirm more specific information in the past inspection information list display area 1202 and presses a "view" button 1207, thereby switching the GUI to display the more specific information or acquired image data.

The operator can add an inspection to the inspection in a transmission suspension state among the inspections indicated in the past inspection information list display area 1202. In this case, the operator selects the inspection which desires the additional imaging operation from the past inspection information list display area 1202 and presses an "inspection resumption" button 1206, thereby allowing the issuance of an instruction to execute the additional imaging operation.

Figure 8:
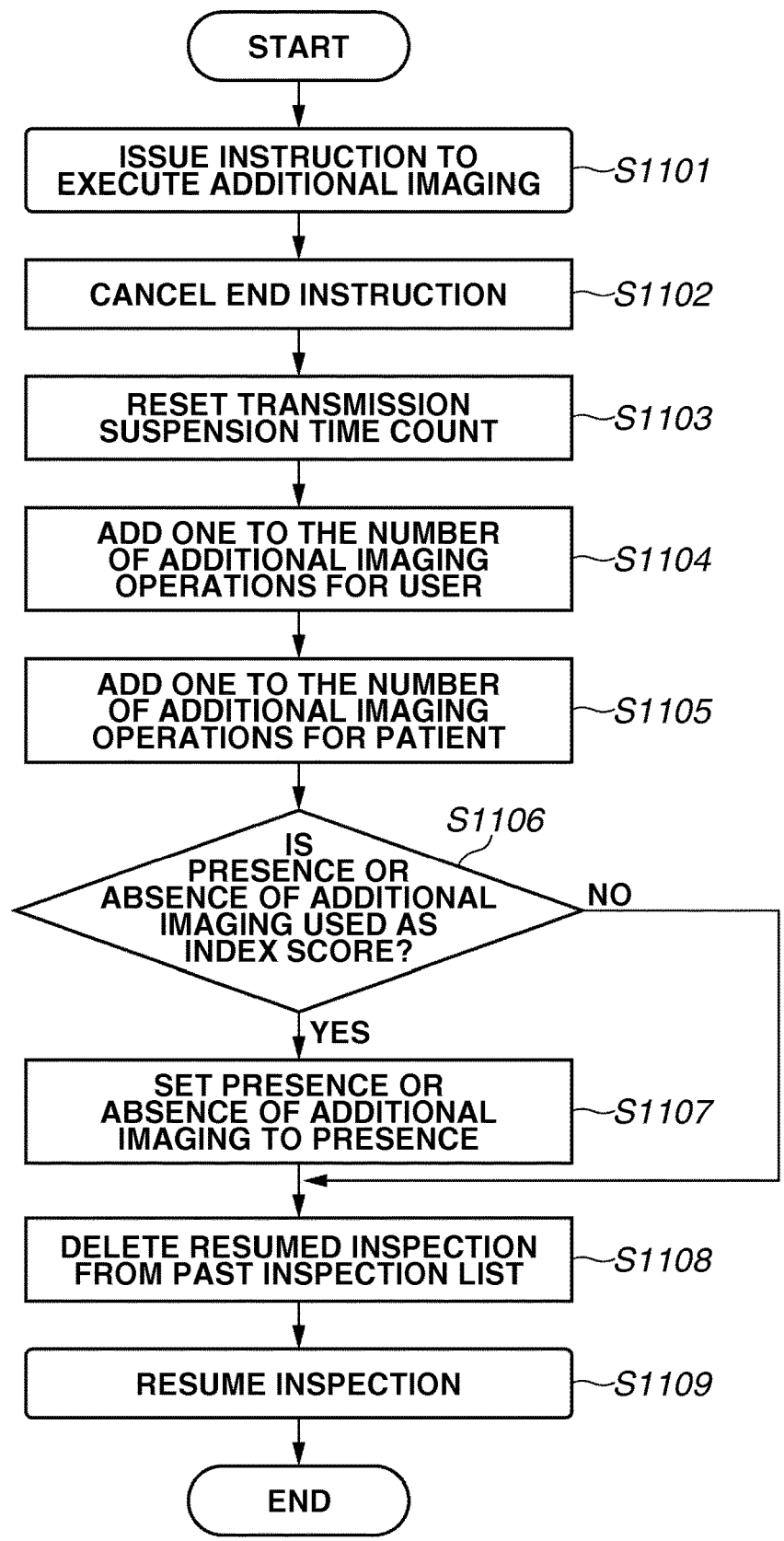
FIG. 8 is a flow chart illustrating an example of operation processing in issuing an instruction to execute an additional imaging operation.

The operation processing of the medical imaging apparatus in instructing the inspection being in a transmission suspension state to execute the additional imaging operation is described below with reference to a flow chart illustrated in FIG. 8. FIG. 8 is the flow chart illustrating an example of operation processing from the issuance of the instruction to execute the additional imaging operation to the resumption of the inspection. The processing is implemented by the CPU 18 of the medical imaging apparatus 303 executing the program stored in the ROM 16.

In step S1101, the imaging execution unit 404 determines that the instruction to execute the additional imaging operation is issued when the operator presses the "inspection resumption" button 1206 as described above. The processing corresponds to the processing returning from step S710 to S703 in the flow chart illustrated in FIG. 4.

In step S1102, the inspection management unit 407 transmits an inspection end instruction cancel request to the end instruction cancel unit 406. The end instruction cancel unit 406 receives the inspection end instruction cancel request and then shifts the inspection in a transmission suspension state to the inspection in an execution state.

In step S1103, the inspection management unit 407 transmits a count reset request to the transmission suspension time counting unit 408. The transmission suspension time counting unit 408 receives the count reset request, ends count on the way and resets count.

In step S1104, the inspection management unit 407 transmits an instruction to add counting to the "unit for counting the number of additional imaging operations for user" 409 and the "unit for counting the number of additional imaging operations for patient 410." The "unit for counting the number of additional imaging operations for user" 409 adds one to the number of additional imaging operations for user according to the instruction to add counting.

In step S1105, the "unit for counting the number of additional imaging operations for patient" 410 similarly adds one to the number of additional imaging operations for patient according to the instruction to add counting.

In step S1106, the inspection management unit 407 notifies the transmission suspension time determination unit 405 of the issuance of the instruction to execute the additional imaging operation. The transmission suspension time determination unit 405 is notified and then determines whether the presence or absence of the addition of imaging is used as an index score by referring to the index storage unit 403. If the presence or absence of the addition of imaging is used as an index score (YES in step S1106), the transmission suspension time determination unit 405 advances the processing to step S1107. If the presence or absence of the addition of imaging is not used as an index score (NO in step S1106), the transmission suspension time determination unit 405 advances the processing to step S1108.

In step S1107, the transmission suspension time determination unit 405 sets the presence or absence of the addition of imaging in inspection information to presence.

In step S1108, the inspection management unit 407 deletes the resumed inspection in the past inspection list displayed by the GUI of the display unit 11 from the past inspection list to update the past inspection list.

In step S1109, the imaging execution unit 404 resumes the inspection.

Thus, the inspection in a transmission suspension state can be resumed according to the operator's instruction to execute the additional imaging operation.

An example of the GUI for confirming and setting the index score used for determining the transmission suspension time and stored in the index storage unit is described below with reference to FIGS. 9, 10, and 11.

Figure 9:
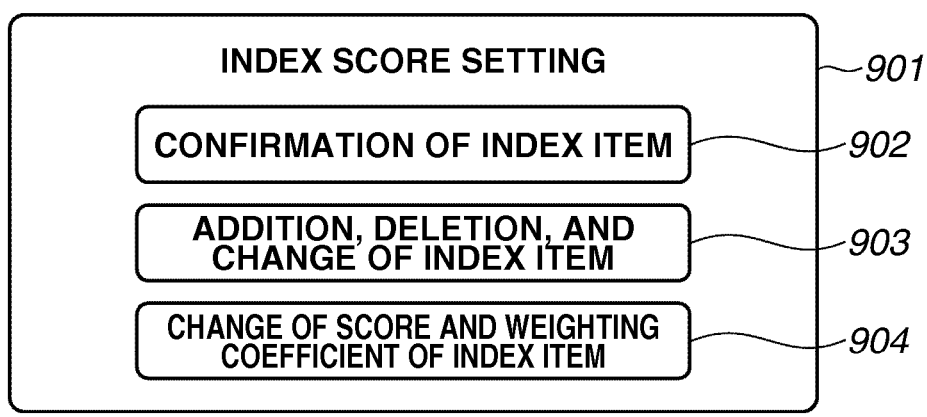
FIG. 9 is a diagram illustrating an example of the initial state of an index score setting screen.

FIG. 9 is a diagram illustrating an example of the initial state of an index score setting screen. The index score setting unit 402 displays an index score setting screen 901 illustrated in FIG. 9 on the display unit 11 according to the operator's instruction to set an index score. In setting the index score, the operator can perform "the confirmation of the index score," "the addition, deletion, and change of the index item," and "the change of score and weighting coefficient of the index item." As described below, the index score setting unit 402 sets the index used for determining the transmission suspension time according to the operator's operation of setting the index used for determining the transmission suspension time.

The index score setting screen 901 displays a button 902 for "the confirmation of the index score," a button 903 for "the addition, deletion, and change of the index item," and a button 904 for "the change of score and weighting coefficient of the index item" corresponding to the abovementioned processing. The operator pressing these buttons causes the index score setting unit 402 to display a corresponding screen.

Figure 10:
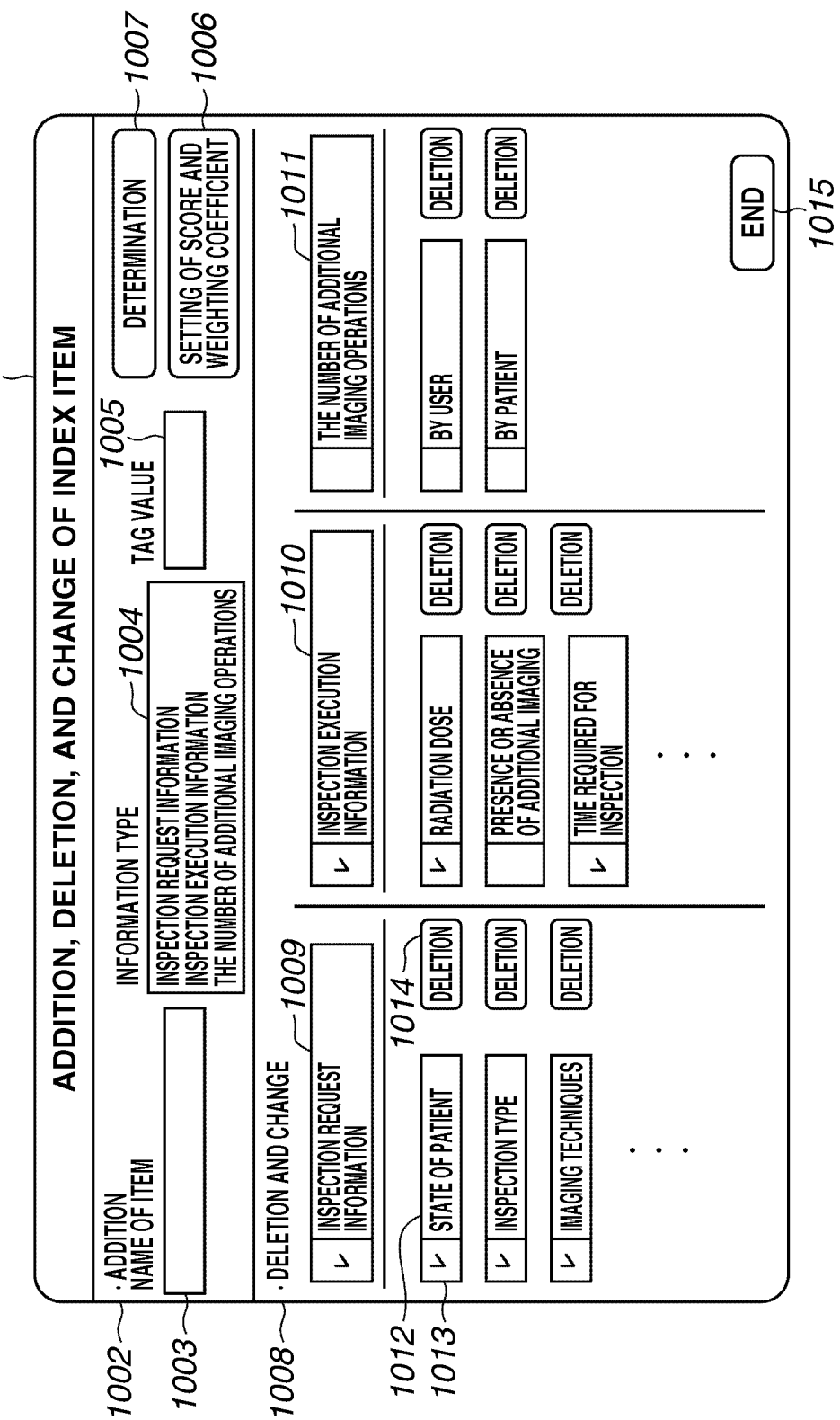
FIG. 10 is a diagram illustrating an example of a screen for setting the addition, deletion, and availability of items used as an index in setting an index score.

FIG. 10 is a diagram illustrating an example of a screen for setting adding, deleting, and availability of items used as an index in setting the index score. The index score setting unit 402 displays an index item editing screen 1001 illustrated in FIG. 10 according to the operator pressing the button 903 for "the addition, deletion, and change of the index item" on the index score setting screen 901 illustrated in FIG. 9. The index item editing screen 1001 includes an index item addition portion 1002 and an index item editing portion 1008.

The index item addition portion 1002 is an area for adding a new index item. When a new index item is added, the operator inputs the name of the index item into an item name input portion 1003 and selects an information type under which the added item falls at an information type selection portion 1004. The operator inputs a tag value for identifying the index item into a tag value input portion 1005. The operator pressing a new addition item determination portion 1007 causes the index score setting unit 402 to add a new index item to input the new index item into the index item editing portion 1008. In this stage, the newly added index item itself is substantially vacant.

For this reason, a score and a weighting coefficient need to be set to the newly added index item.

When a score and a weighting coefficient need to be set to the newly added index item, the operator presses a score and weighting coefficient setting portion 1006. Thereby the index score setting unit 402 displays a score and weighting coefficient setting screen. If there exists an index item to which a score and a weighting coefficient are not yet set when the operator presses an index item editing end portion 1015, the index score setting unit 402 forcibly displays the score and weighting coefficient setting screen to urge the operator to set a score and a weighting coefficient. The score and weighting coefficient setting screen is described below with reference to FIG. 11.

The index item editing portion 1008 is an area for deleting and changing the currently set index score. The change of an index item refers to the change of setting as to whether the currently set index item is actually used as an index item without being deleted. The index item editing portion 1008 displays an inspection request information setting portion 1009, an inspection execution information setting portion 1010, "a portion for setting the number of additional imaging operations 1011," an index item display portion 1012, an index item selection portion 1013, an index item deletion instruction portion 1014, and an index item editing end portion 1015.

The inspection request information setting portion 1009, the inspection execution information setting portion 1010, and "the portion for setting the number of additional imaging operations 1011" are areas for setting whether respective information types are collectively used as index items. The operator checks check boxes on the left side of the names of the respective information types to cause the index score setting unit 402 to perform setting so that all the index items included in the information type can be used. However, even if the information type is checked, the index score setting unit 402 performs setting whether to use index items for each index item by the operator checking or unchecking the check boxes of the index item selection portion 1013.

The index score setting unit 402 performs setting so that all the index items included in the information type cannot be used by the operator unchecking the check boxes on the left side of the names of the respective information types. In this case, however, the operator cannot set whether to use index items for each index item.

The index item deletion instruction portion 1014 is displayed in correspondence to the index item display portion 1012. The operator pressing the index item deletion instruction portion 1014 causes the index score setting unit 402 to delete the index item registered to the index storage unit 403 and delete the corresponding index item from the index item editing portion 1008. Finally, the operator pressing the index item editing end portion 1015 causes the index score setting unit 402 to shift the display from the index item editing screen 1001 to the index score setting screen 901.

Figure 11:
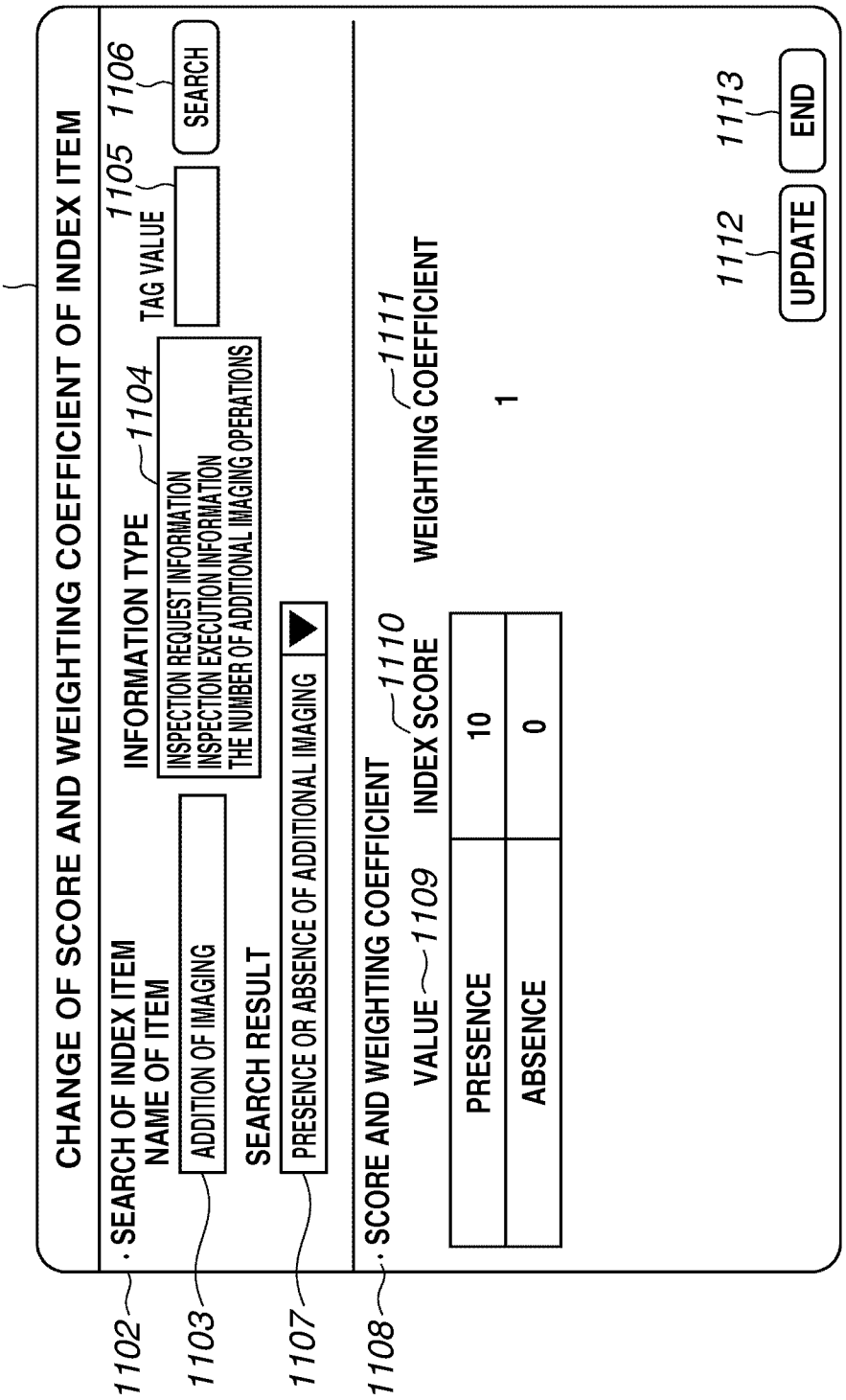
FIG. 11 is a diagram illustrating an example of a score and weighting coefficient setting screen for setting a score and a weighting coefficient.

FIG. 11 is a diagram illustrating an example of a score and weighting coefficient setting screen. The operator pressing the button 902 of "the confirmation of the index item" or the button 904 of "the change of score and weighting coefficient of the index item" on the index score setting screen 901 illustrated in FIG. 9 causes the index score setting unit 402 to display an index item score editing screen 1101 illustrated in FIG. 11. The index item score editing screen 1101 includes an index item search portion 1102 and an index item score setting portion 1108.

The index item search portion 1102 is an area for searching the currently set index items. When searching index items, the operator inputs characters or values to any of an item name input portion 1103, an information type selection portion 1104, and a tag value input portion 1105 and then presses a search execution instruction portion 1106. Thereby, the index score setting unit 402 executes searching for the index items stored in the index storage unit 403 using the input search conditions. If the operator inputs a plurality of search conditions, the index score setting unit 402 executes searching with an AND search. A search result display portion 1107 displays the index item hit with the search. The operator selecting the index item displayed on the search result display portion 1107 causes the index score setting unit 402 to display the score set to the index item and the index item on the index item score setting portion 1108.

The index item score setting portion 1108 includes a set value displaying and setting portion 1109, an index score displaying and setting portion 1110, a weighting coefficient setting and displaying portion 1111, an update execution instruction portion 1112, and an index item score editing end portion 1113. The set value displaying and setting portion 1109, the index score displaying and setting portion 1110, and the weighting coefficient setting and displaying portion 1111 display the set value, the score and the weighting coefficient set to the index item selected on the search result display portion 1107. However, when the operator presses the button 902 of "the confirmation of the index item" on the index score setting screen 901 illustrated in FIG. 9, display only for confirmation purpose is made. In other words, the set value displaying and setting portion 1109, the index score displaying and setting portion 1110, and the weighting coefficient setting and displaying portion 1111 display only the set value, so that the operator cannot change the value.

When the operator presses the button 904 of "the change of score and weighting coefficient of the index item" on the index score setting screen 901 illustrated in FIG. 9, the operator can delete the set value on the set value displaying and setting portion 1109. Furthermore, the operator can change the set value on the index score displaying and setting portion 1110 and the weighting coefficient setting and displaying portion 1111. The operator performing change on the set value displaying and setting portion 1109, the index score displaying and setting portion 1110, and the weighting coefficient setting and displaying portion 1111 and pressing the update execution instruction portion 1112 causes the index score setting unit 402 to store the change into the index storage unit 403. Finally, the operator pressing the index item score editing end portion 1113 causes the index score setting unit 402 to shift display from the index item score editing screen 1101 to the index score setting screen 901. Thus, the setting of the index item, the score and the weighting coefficient is made changeable to allow setting a flexible method of determining the transmission suspension time to which an operation system for each facility is applied.

The configuration and operation of a medical imaging apparatus according to a second exemplary embodiment of the present invention is described below. The first exemplary embodiment the inspection end notification is not transmitted unless the transmission suspension time has passed. Thus, a case where accounting is urgently desired cannot be achieved. The second exemplary embodiment described below can perform accounting in the intra-hospital information system as required even in the transmission suspension state in which the inspection end notification is not transmitted to the intra-hospital information system.

An internal configuration of the medical imaging apparatus according to the second exemplary embodiment is described below with reference to FIG. 12.

Figure 12:
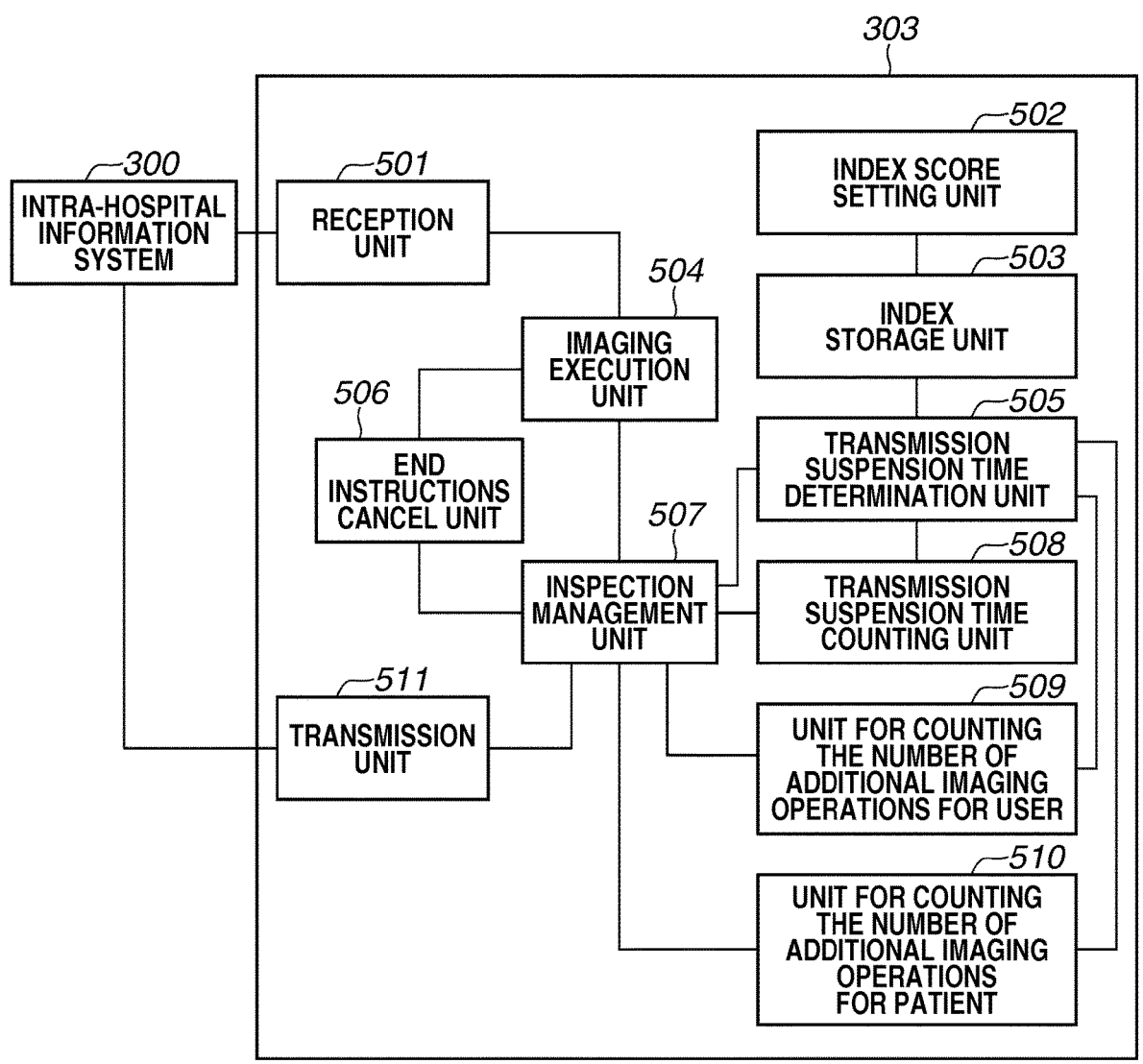
FIG. 12 is a block diagram illustrating an example of an internal configuration of a medical imaging apparatus according to a second exemplary embodiment of the present invention.

FIG. 12 is a block diagram illustrating an example of the internal configuration of the medical imaging apparatus. The medical imaging apparatus 303 according to the present exemplary embodiment is similar in configuration to that in the first exemplary embodiment illustrated in FIG. 3. The components 501 to 511 of the medical imaging apparatus 303 illustrated in FIG. 12 correspond to the components 401 to 411 of the medical imaging apparatus 303 illustrated in FIG. 3. Accordingly, description of components 501 to 511 is omitted to avoid unnecessary duplication.

In the first exemplary embodiment, the transmission suspension time is calculated for each inspection and the inspection end notification is merely transmitted after counting is ended. The present exemplary embodiment enables transmitting the inspection end information about the inspection irrespective of a counting state if the inspection end information is not yet transmitted in the case where accounting is desired in the intra-hospital information system 300. In other words, in the present exemplary embodiment, the reception unit 501 receives not only the inspection request information but also the accounting request transmitted from the intra-hospital information system 300.

The operation processing of the medical imaging apparatus according to the present exemplary embodiment is described below with reference to FIG. 13.

Figure 13:
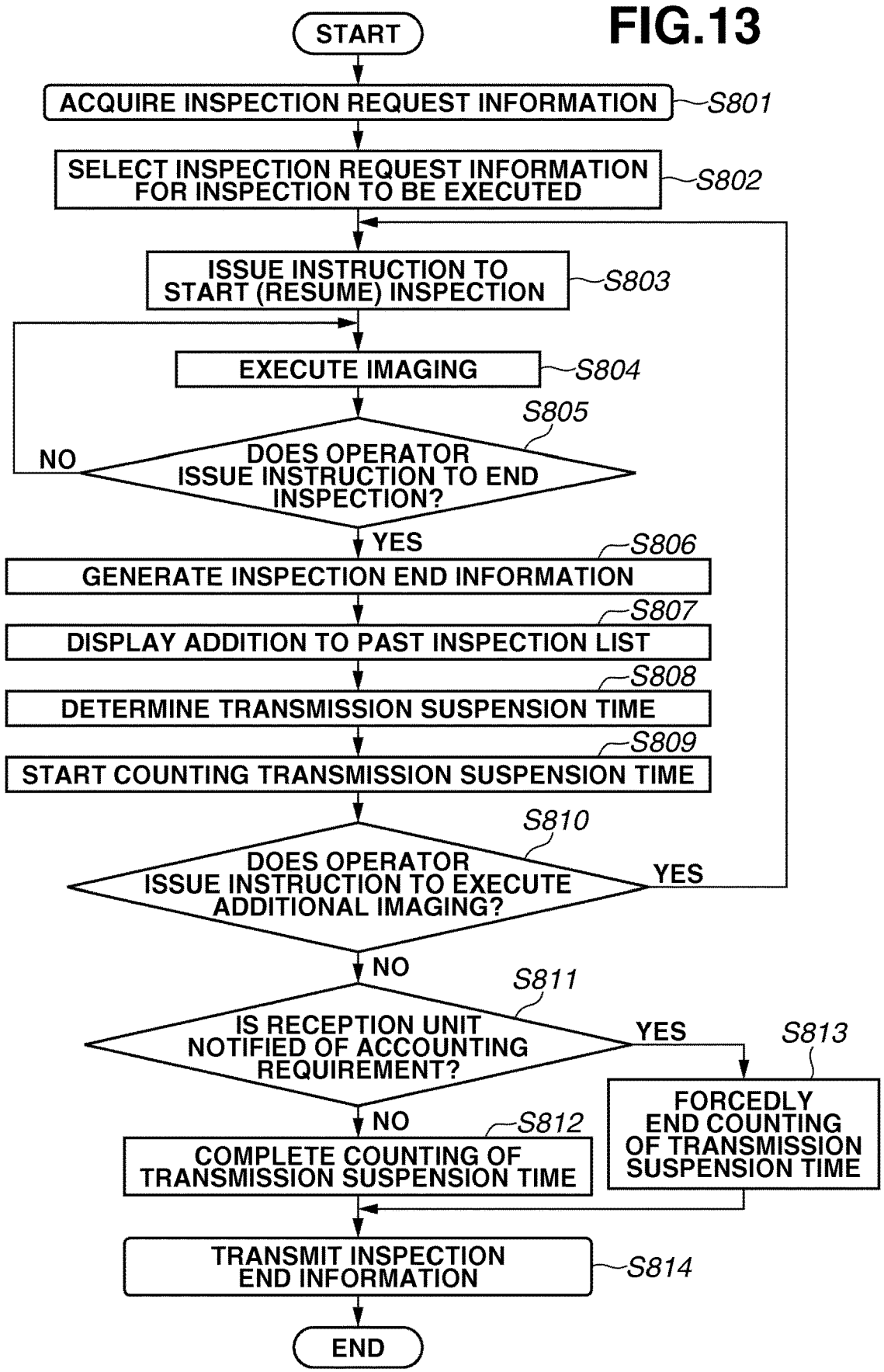
FIG. 13 is a flow chart illustrating an example of the operation processing of the medical imaging apparatus according to the second exemplary embodiment.

FIG. 13 is a flow chart illustrating an example of the operation processing performed from the time of reception of the inspection request information to the time of transmission of the inspection end notification. The processing is implemented by the CPU 18 of the medical imaging apparatus 303 executing the program stored in the ROM 16.

Steps S801 to S810 in the flow chart illustrated in FIG. 13 are similar to steps S701 to S710 in FIG. 4 of the first exemplary embodiment. For this reason, the processing only in step S811 and following steps is described.

In step S811, the reception unit 501 determines whether the intra-hospital information system 300 notifies the reception unit 501 of accounting request while the transmission suspension time counting unit 508 is counting a transmission suspension time. In other words, the reception unit 501 determines whether the intra-hospital information system 300 notifies the reception unit 501 of accounting request before the inspection management unit 507 receives the counting end notification of the transmission suspension time. If the intra-hospital information system 300 notifies the reception unit 501 of the accounting request (YES in step S811), the processing proceeds to step S813.

In step S813, the reception unit 501 is notified of the accounting request by the intra-hospital information system 300. The reception unit 501 transmits the accounting request to the inspection management unit 507 via the imaging execution unit 504. When the inspection management unit 507 receives the accounting request, the inspection management unit 507 confirms that the inspection in which accounting is requested is in a transmission suspension state. After the confirmation, the inspection management unit 507 issues an instruction to forcibly end counting to the transmission suspension time counting unit 508 and shifts the state of the inspection from a transmission suspension state to an end state. The transmission suspension time counting unit 508 receives the instruction to forcibly end counting and then ends counting of the transmission suspension time of the inspection subjected to the instruction.

In step S814, the inspection management unit 507 issues an instruction to transmit the inspection end notification, the inspection end information, and the image data of the inspection rendered to the end state to the transmission unit 511. The transmission unit 511 transmits the inspection end notification, to which the inspection end information is added, and the image data to the intra-hospital information system 300 corresponding thereto.

The inspection management unit 507 updates the past inspection list displayed by the GUI on the display unit 11. More specifically, the inspection management unit 507 changes indication in the column of "inspection end information notification" of the inspection the state of which is shifted to the end state in the past inspection list to "Ended."

On the other hand, if the reception unit 501 does not receive the accounting request (NO in step S811), the processing proceeds to step S812. The processing in step S812 is similar to that in step S711 of the flow chart of the first exemplary embodiment illustrated in FIG. 4, so that the description thereof is omitted.

In the present exemplary embodiment, the resumption of the inspection according to the instruction to execute an additional imaging operation may be repeated over and over again until the counting of the transmission suspension time is ended or the accounting request is transmitted from the intra-hospital information system 300.

Thus, according to the present exemplary embodiment, if the accounting request is transmitted from the intra-hospital information system 300, the counting of the transmission suspension time is forcibly ended and the inspection end notification, to which the inspection end information is added, and the image data are transmitted to the intra-hospital information system 300 corresponding thereto. Consequently, the intra-hospital information system 300 can quickly perform accounting.

The configuration and operation of a medical imaging apparatus according to a third exemplary embodiment of the present invention is described below. In the foregoing exemplary embodiments, if the operator turns off the power supply of the medical imaging apparatus during the transmission suspension state where the inspection end notification is not transmitted to the intra-hospital information system, the inspection end notification remains untransmitted, so that the intra-hospital information system cannot perform post-processing. In the third exemplary embodiment, even if the operator turns off the power supply of the medical imaging apparatus in the transmission suspension state where the inspection end notification is generally not transmitted to the intra-hospital information system, the inspection end notification can be transmitted to the intra-hospital information system.

An internal configuration of the medical imaging apparatus according to the third exemplary embodiment is described below with reference to FIG. 14.

Figure 14:
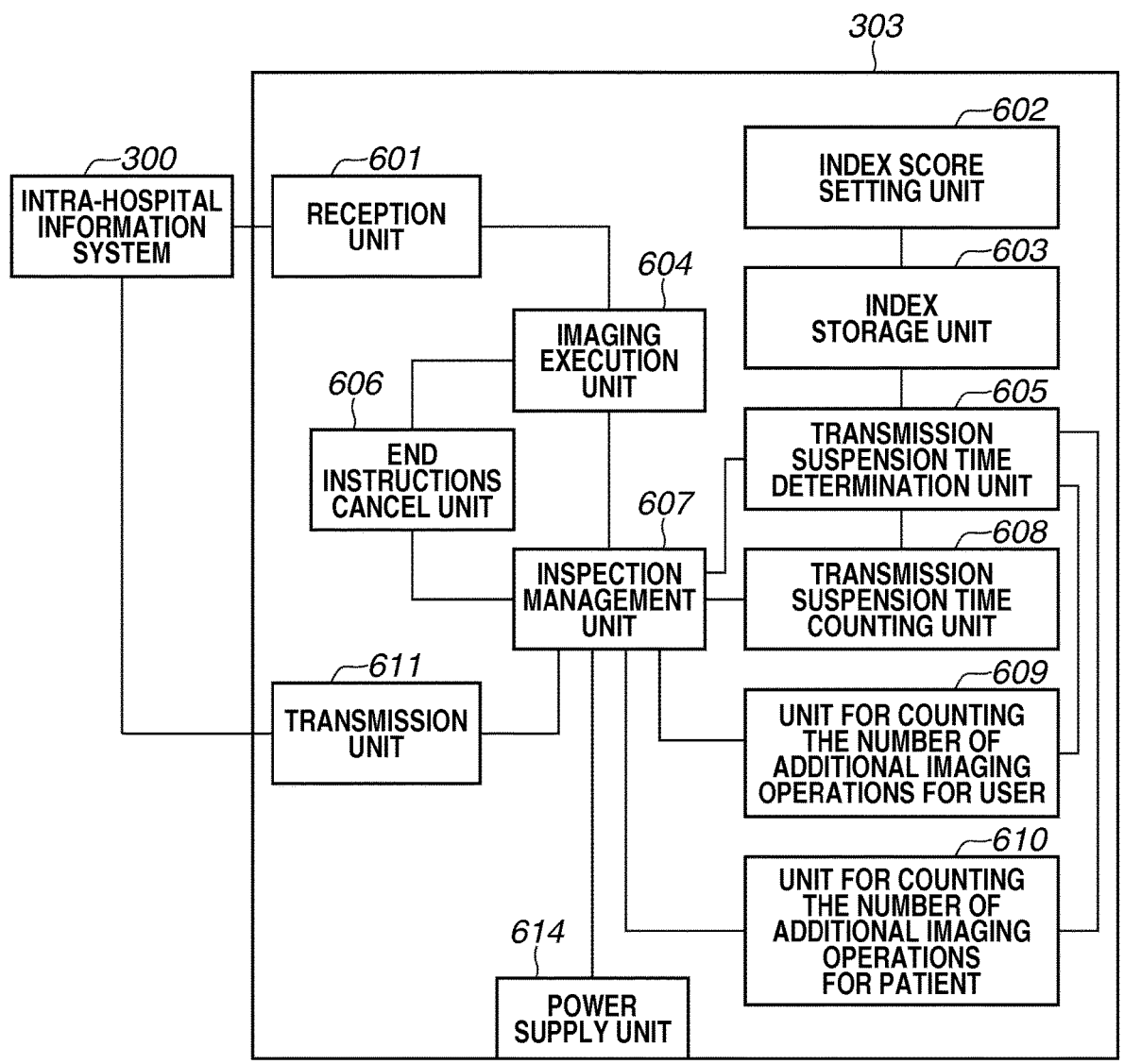
FIG. 14 is a block diagram illustrating an example of an internal configuration of a medical imaging apparatus according to a third exemplary embodiment of the present invention.

FIG. 14 is a block diagram illustrating an example of the internal configuration of the medical imaging apparatus. The medical imaging apparatus 303 according to the present exemplary embodiment is substantially similar in configuration to that in the first exemplary embodiment illustrated in FIG. 3, but different from the first exemplary embodiment in that the medical imaging apparatus 303 includes a power supply unit 614. The components 601 to 611 of the medical imaging apparatus 303 illustrated in FIG. 14 correspond to the components 401 to 411 of the medical imaging apparatus 303 illustrated in FIG. 3. Accordingly, description thereof is omitted to avoid unnecessary duplication.

The power supply unit 614 is attached to the medical imaging apparatus 303 and turns on and off the medical imaging apparatus 303. When the power supply unit 614 switches the medical imaging apparatus 303 from the on state to the off state, the power supply unit 614 transmits a power supply OFF notification to the inspection management unit 607. When the inspection management unit 607 receives the power supply OFF notification, the inspection management unit 607 causes the transmission unit 611 to forcibly transmit the inspection end notification of the inspection in the transmission suspension state to the intra-hospital information system 300 irrespective of a counting state of the transmission suspension time.

Figure 15:
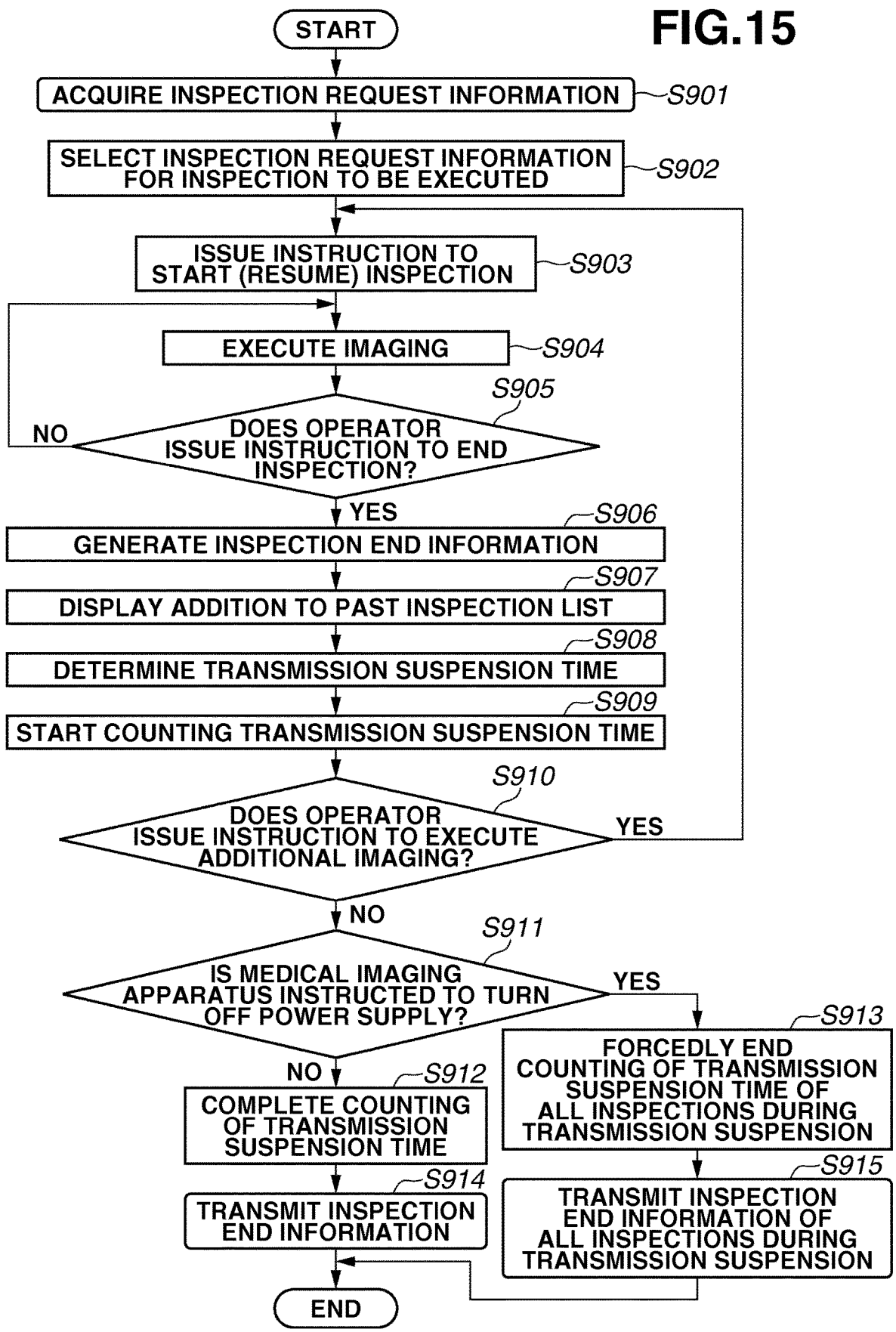
FIG. 15 is a flow chart illustrating an example of the operation processing of the medical imaging apparatus according to the third exemplary embodiment.

The operation processing of the medical imaging apparatus according to the present exemplary embodiment is described below with reference to FIG. 15. FIG. 15 is a flow chart illustrating an example of the operation processing performed from the time of reception of the inspection request information to the time of transmission of the inspection end notification. The processing is implemented by the CPU 18 of the medical imaging apparatus 303 executing the program stored in the ROM 16.

Steps S901 to S910 in the flow chart illustrated in FIG. 15 are similar to steps S701 to S710 in FIG. 4 of the first exemplary embodiment. For this reason, the processing only in step S911 and following steps is described.

In step S911, the power supply unit 614 determines whether the operator issues an instruction to turn off the power supply of the medical imaging apparatus 303 while the transmission suspension time counting unit 608 is counting a transmission suspension time. In other words, the power supply unit 614 determines whether the operator issues an instruction to turn off the power supply of the medical imaging apparatus 303 before the inspection management unit 607 receives the counting end notification of the transmission suspension time. If the operator issues the instruction to turn off the power supply (YES in step S911), the processing proceeds to step S913.

In step S913, the power supply unit 614 transmits the power supply OFF notification to the inspection management unit 607 before turning off the power supply. The inspection management unit 607 receives the power supply OFF notification and then issues an instruction to forcibly end counting to the transmission suspension time counting unit 608. The inspection management unit 607 issues an instruction to forcibly end counting to the transmission suspension time counting unit 608 and shifts the state of all inspections in which the transmission suspension time is counted from a transmission suspension state to an end state. The transmission suspension time counting unit 608 receives the instruction to forcibly end counting and then ends the counting of the transmission suspension time of the inspection subjected to the instruction.

In step S915, the inspection management unit 607 instructs the transmission unit 611 to transmit the inspection end notification, the inspection end information, and the image data of all inspections rendered to the end state for each inspection to the transmission unit 611. The transmission unit 611 receives the instruction for transmission and then transmits the inspection end notification, to which the inspection end information is added, and the image data to the intra-hospital information system 300 corresponding thereto.

The transmission unit 611 confirms that the inspection end notification of all inspections is transmitted and then transmits the transmission end notification to the power supply unit 614 via the inspection management unit 607. The power supply unit 614 receives the transmission end notification and then turns off the power supply of the medical imaging apparatus 303.

The inspection management unit 607 updates the past inspection list displayed by the GUI on the display unit 11. More specifically, the inspection management unit 607 changes indication in the column of "inspection end information notification" of the inspection the state of which is shifted to the end state in the past inspection list to "Ended."

On the other hand, if the power supply unit 614 does not determine that the operator issues an instruction to turn off the power supply (NO in step S911), the processing proceeds to steps S912 and S914. The processing in steps S912 and S914 is similar to that in steps S711 and S712 of the flow chart of the first exemplary embodiment illustrated in FIG. 4, so that the description thereof is omitted.

The flow chart illustrated in FIG. 15 describes the case where the timing at which the operator issues the instruction to turn off the power supply of the medical imaging apparatus 303 is determined after the processing in step S910, but the timing is not limited to this case. In other words, irrespective of the timing at which the operator issues the instruction, the power supply unit 614 determines that the operator issues the instruction to turn off the power supply of the medical imaging apparatus 303, and thereafter, the processing proceeds to steps S913 and S915 and the aforementioned processing is performed.

In the present exemplary embodiment, the resumption of the inspection according to the instruction to execute an additional imaging operation may be repeated over and over again until the counting of the transmission suspension time is ended or the power supply of the medical imaging apparatus 303 is turned off.

Thus, according to the present exemplary embodiment, even if the power supply of the medical imaging apparatus 303 is turned off, the inspection end notification of the inspection being in the transmission suspension state is transmitted to the intra-hospital information system 300 to allow preventing the inspection end notification from not being transmitted.

The configuration and operation of a medical imaging apparatus according to a fourth exemplary embodiment of the present invention is described below.

In the forgoing exemplary embodiments, even though the operator wants to examine the image data of the inspection in the transmission suspension state using a high-resolution image storage display apparatus, the image data is not transmitted to the image storage and display apparatus unless the transmission suspension time passes. For this reason, the operator cannot quickly examine the image data. In the present exemplary embodiment, the timing of transmitting the image data and the inspection end notification is made different therebetween to enable the operator to quickly examine the image data and determine whether to execute an additional imaging operation.

An internal configuration of the medical imaging apparatus according to the fourth exemplary embodiment is described below with reference to FIG. 16.

Figure 16:
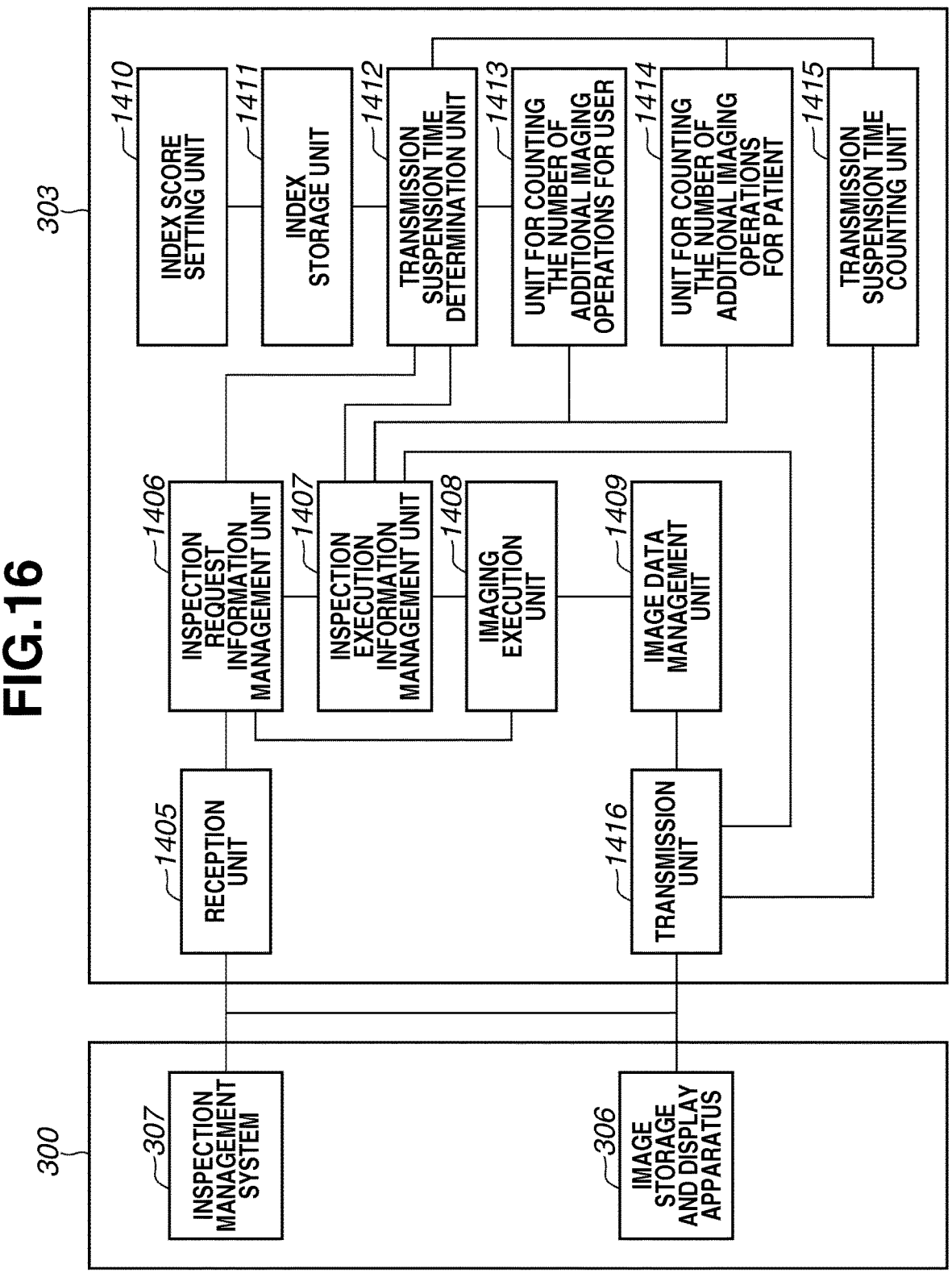
FIG. 16 is a block diagram illustrating an example of an internal configuration of a medical imaging apparatus according to a fourth exemplary embodiment of the present invention.

FIG. 16 is a block diagram illustrating an example of the internal configuration of the medical imaging apparatus. The functional configuration of the medical imaging apparatus illustrated in FIG. 16 is implemented by the CPU 18 executing the program stored in the ROM 16 and the internal storage device 19. In FIG. 16, the HIS 301 and the RIS 302 are consolidated into an inspection management system 307. The inspection management system 307 and the image storage and display apparatus 306 are consolidated into the intra-hospital information system 300. In FIG. 16, although the image storage and display apparatus 306 is used, an image display apparatus for merely displaying image data may be used.

A reception unit 1405 communicates with the inspection management system 307 and the image storage and display apparatus 306 and in particular receives the inspection request information.

An inspection request information management unit 1406 receives the inspection request information from the reception unit 1405 and manages the inspection request information. The inspection request information management unit 1406 displays the inspection request list on the GUI of the display unit 11 and receives the inspection start notification and the inspection end notification of the inspection request information stored therein from the imaging execution unit 1408. When the inspection request information management unit 1406 receives the inspection end notification, the inspection request information management unit 1406 receives the inspection execution information including the execution contents of the inspection.

The inspection request information management unit 1406 receives the inspection execution information and then generates the inspection end information of which the inspection management system 307 is notified using corresponding inspection request information and the inspection execution information.

The inspection execution information management unit 1407 receives the inspection request information and manages execution state of each inspection: the inspection being not yet executed; being executed; in a transmission suspension state; being ended; or being resumed; in collaboration with the imaging execution unit 1408. The state where the inspection is not yet executed refers to the state where the inspection is never started after the reception of the inspection request information. The state where the inspection is being executed refers to the state where an imaging operation is executed by the medical imaging apparatus 303. The transmission suspension state refers to the state where the inspection is executed once, an instruction to end the inspection is issued after the inspection is started and the inspection end notification is suspended. The state where the inspection is ended refers to the state where the determined transmission suspension time passes and the inspection end information and the image storage request are transmitted to the intra-hospital information system 300. The state where the inspection is resumed refers to the state where an instruction to execute an additional imaging operation is issued to the inspection in the transmission suspension state and an imaging operation is executed by the medical imaging apparatus 303. The inspection execution information management unit 1407 manages a state of all the inspection request information stored in the medical imaging apparatus 303 to play a role to maintain consistency. The inspection execution information management unit 1407 includes an arithmetic unit and a main storage unit such as a CPU and a program controlling the units.

An imaging execution unit 1408 executes an imaging operation according to the instruction of the operator. The imaging execution unit 1408 notifies the inspection request information management unit 1406 and the inspection execution information management unit 1407 of the operator's instruction to start the inspection and instruction to end the inspection. The imaging execution unit 1408 received the instruction to end the inspection and then transmits the acquired image data to an image data management unit 1409.

The imaging execution unit 1408 is connected to an external user interface such as a mouse controller and a keyboard. The imaging execution unit 1408 controls the GUI displayed on the display unit 11 of the medical imaging apparatus 303 according to the operation of the operator.

The image data management unit 1409 manages the image data acquired by executing the inspection. More specifically, the image data management unit 1409 stores the image data received from the imaging execution unit 1408, transmits the image data to the transmission unit 1416 and instructs the transmission unit 1416 to transmit the image data.

The transmission unit 1416 communicates with the intra-hospital information system 300 and particularly transmits the inspection end information, the image storage request, and the acquired image data.

A transmission suspension time management unit 1412 receives the inspection request information, patient information, inspection execution information, information about the number of additional imaging operations for operator, and information about the number of additional imaging operations for patient. The transmission suspension time management unit 1412 calculates an index score by referring to an index storage unit 1411 to determine a transmission suspension time of the image storage request and a transmission suspension time of the inspection end information for each inspection.

A transmission suspension time counting unit 1415 starts counting according to an instruction to start counting issued from the transmission suspension time management unit 1412. The transmission suspension time counting unit 1415 counts a transmission suspension time and then transmits a counting end notification to the transmission unit 1416. In the present exemplary embodiment, although the transmission suspension time counting unit 1415 is included in the medical imaging apparatus 303, in another alternative, the transmission suspension time counting unit 1415 may be directly connected to the medical imaging apparatus 303 from the outside using a connection interface such as USB, for example.

A "unit for counting the number of additional imaging operations for user" 1413 counts the number of additional imaging operations for each operator using user information of the operator stored inside each time the "unit for counting the number of additional imaging operations for user" 1413 is notified of the additional imaging operation by the inspection execution information management unit 1407.

A "unit for counting the number of additional imaging operations for patient" 1414 counts the number of additional imaging operations for each patient using patient information stored inside each time the "unit for counting the number of additional imaging operations for patient" 1414 is notified of the additional imaging operation by the inspection execution information management unit 1407.

The index storage unit 1411 stores: each item included in the inspection request information, patient information, inspection execution information, information about the number of additional imaging operations for user, and information about the number of additional imaging operations for patient; index scores set thereto; and a weighting coefficient for each item. The index storage unit 1411 includes the internal storage device 19 and a program for controlling the internal storage device 19. In the present exemplary embodiment, although the index storage unit 1411 is included in the medical imaging apparatus 303, in another alternative, the index storage unit 1411 may be directly connected to the medical imaging apparatus 303 from the outside using a connection interface such as USB, for example. The index storage unit 1411 may be comprised of an information storage server to be connected to a plurality of the medical imaging apparatus 303 via the network. The plurality of the medical imaging apparatus 303 shares the index storage unit 1411 therebetween via the network to eliminate the need for setting the index scores in each medical imaging apparatus 303, facilitating the management of index scores, which enables the improvement of consistency between the index scores.

An index score setting unit 1410 determines whether each item stored in the index storage unit 1411 is used as an index score. If each item is used, the index score setting unit 1410 changes the score and the value of weighting coefficient for each item.

Figure 17:
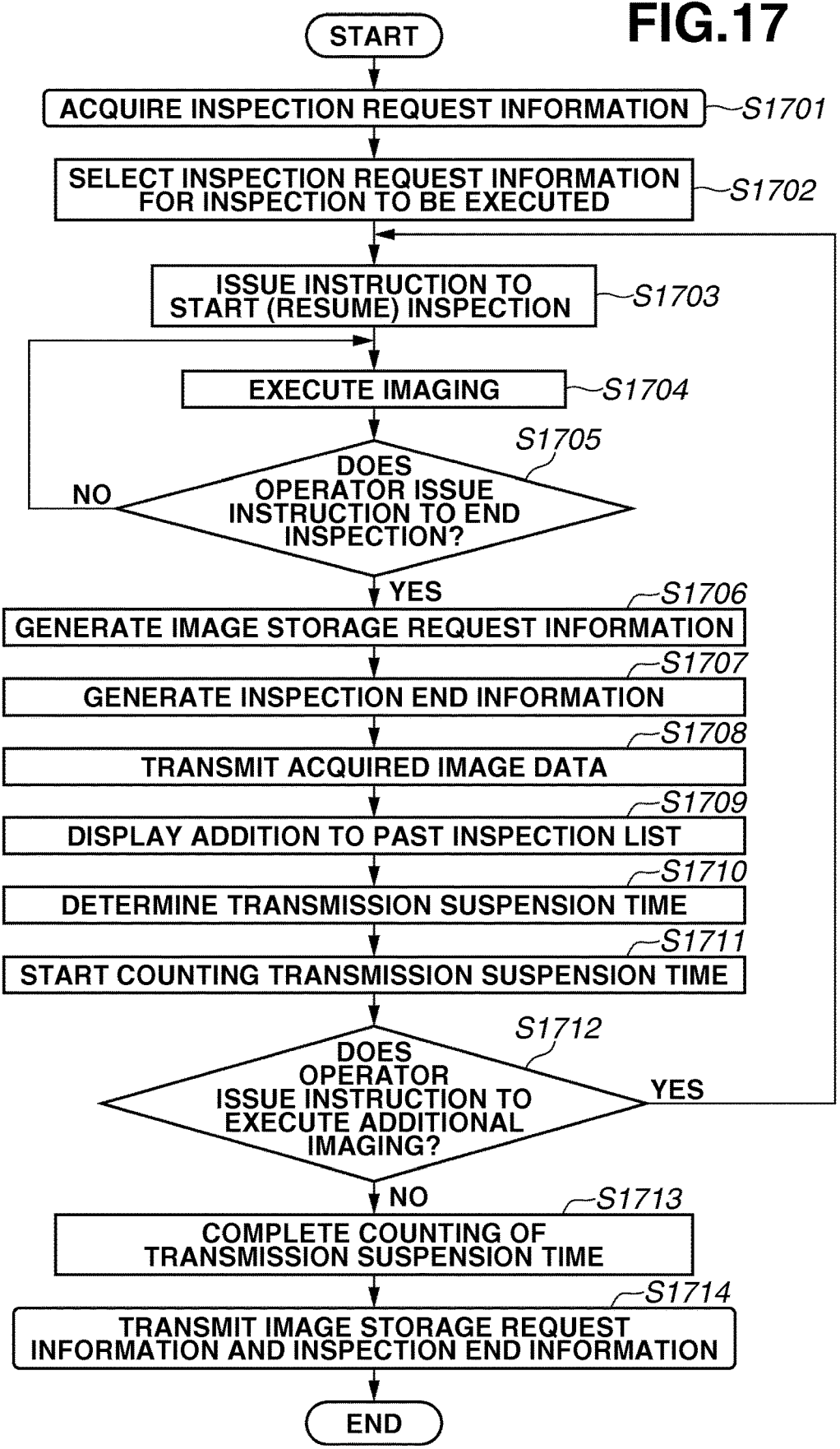
FIG. 17 is a flow chart illustrating an example of the operation processing of the medical imaging apparatus according to the fourth exemplary embodiment.

The operation processing of the medical imaging apparatus according to the present exemplary embodiment is described below with reference to the flow chart illustrated in FIG. 17. FIG. 17 is a flow chart illustrating an example of the operation processing performed from the time of reception of the inspection request information to the time of transmission of the inspection end notification. The processing is implemented by the CPU 18 of the medical imaging apparatus 303 executing the program stored in the ROM 16.

In step S1701, the transmission unit 1416 requests the inspection management system 307 to transmit the inspection request information via the network. The request is made when the operator mainly presses the acquisition instruction button for the inspection request information displayed by the GUI on the display unit 11 of the medical imaging apparatus 303. Alternatively, the transmission unit 1416 may automatically make a request every predetermined time interval or may make a request at the timing at which the operator issues an instruction to display the inspection request information as a list. The timing is not limited only to the above.

When the transmission of the inspection request information is requested, an acquisition condition can be set to an item included in the inspection request information. In other words, the transmission unit 1416 requests the inspection management system 307 with at least one acquisition condition input. In this case, the inspection management system 307 extracts the inspection request information in which an inspection is not yet started and which matches with the acquisition condition from the stored inspection request information and transmits the inspection request information to the medical imaging apparatus 303. The reception unit 1405 receives the returned inspection request information. The reception unit 1405 then transmits the acquired inspection request information to the inspection request information management unit 1406. The inspection request information management unit 1406 lists the received inspection request information to display the list on the display unit 11 with the GUI and stores the inspection request information in the internal storage device 19.

In step S1702, the operator selects the inspection request information to be executed from the inspection request information displayed as the list. The inspection request information management unit 1406 switches the inspection request information selected by the operator to detailed information and displays the detailed information. The operator may select not only one piece of inspection request information corresponding to the inspection to be executed from the inspection request information displayed on the list but also a plurality of inspections. In other words, the medical imaging apparatus 303 can start the inspections in the selected inspection request information at the same time.

In step S1703, the operator presses the inspection start button displayed by the GUI on the display unit 11.

In step S1704, the imaging execution unit 1408 starts inspection based on the inspection request information selected according to the operator's instruction to start the inspection. At this point, the imaging execution unit 1408 instructs the transmission unit 1416 via the inspection execution information management unit 1407 to send the inspection start notification to the inspection management system 307. At this point, the inspection execution information management unit 1407 shifts the state of the sent inspection request information from the state where the inspection is not yet executed to the state where the inspection is being executed. The transmission unit 1416 transmits the inspection start notification to the inspection management system 307. After that, the imaging execution unit 1408 repetitively executes imaging operations according to the operator's instruction to execute the imaging operations.

In step S1705, the imaging execution unit 1408 determines whether the operator issues an instruction to end the inspection. The operator presses the inspection end button displayed by the GUI on the display unit 11 when the operator ends all the imaging operations and the post processing required for the inspection. If the imaging execution unit 1408 receives the operator's instruction to end the inspection (YES in step S1705), the imaging execution unit 1408 advances the processing to step S1706. If the imaging execution unit 1408 does not receive the operator's instruction to end the inspection (NO in step S1705), the imaging execution unit 1408 returns the processing to step S1704.

In step S1706, the imaging execution unit 1408 ends the inspection being executed and generates the inspection execution information from the inspection execution result. Thereafter, the imaging execution unit 1408 transmits the inspection end notification and the inspection execution information to the inspection request information management unit 1406 via the inspection execution information management unit 1407. The inspection request information management unit 1406 receives the inspection end notification and then generates image storage request information to be transmitted to the image storage and display apparatus 306 using the patient information included in the inspection request information, the inspection execution information, and the inspection request information.

In step S1707, the inspection request information management unit 1406 generates the inspection end information which is attached to the inspection end notification to be transmitted to the inspection management system 307 using the patient information included in the inspection request information, the inspection execution information, and the inspection request information. The operation processing in steps S1706 and S1707 stated above may be carried out at the same time or may be opposite in order.

In step S1708, the inspection execution information management unit 1407 shifts the state of the sent inspection request information from the state where the inspection is being executed to the state where a transmission is suspended. The imaging execution unit 1408 transmits the acquired image data to the image data management unit 1409. The image data management unit 1409 receives the image data and then storages the image data in the internal storage device 19 and transmits the image data to the transmission unit 1416. The transmission unit 1416 receives the image data and then directly transmits the image data to the image storage and display apparatus 306 via the network. For this reason, the operator can instantly examine the image data via the image storage and display apparatus 306.

In step S1709, the inspection execution information management unit 1407 adds a part of the generated inspection end information to the past inspection information list displayed by the GUI on the display unit 11 and displays the list. The GUI displaying an inspection being in the state where a transmission is suspended on the past inspection information list is similar to that illustrated in FIG. 7.

In step S1710, the inspection request information management unit 1406 transmits the inspection request information and the inspection execution information to the transmission suspension time management unit 1412. The transmission suspension time management unit 1412 receives the inspection request information and the inspection execution information. The inspection execution information management unit 1407 instructs the "unit for counting the number of additional imaging operations for user" 1413 and the "unit for counting the number of additional imaging operations for patient" 1414 to transmit the number of additional imaging operations. The "unit for counting the number of additional imaging operations for user" 1413 and the "unit for counting the number of additional imaging operations for patient" 1414 receive the instruction to transmit the number of additional imaging operations and then transmit the information about the number of additional imaging operations stored therein to the transmission suspension time management unit 1412. The transmission suspension time management unit 1412 receives the inspection request information, the inspection execution information, information about the number of additional imaging operations for user, and information about the number of additional imaging operations for patient. The transmission suspension time management unit 1412 determines a transmission suspension time of the inspection end information and the image storage request using the foregoing method of determining a transmission suspension time.

In step S1711, the transmission suspension time management unit 1412 transmits an instruction to start counting to the transmission suspension time counting unit 1415. The transmission suspension time counting unit 1415 receives the instruction to start counting and starts counting at the same time. When the transmission suspension time counting unit 1415 ends counting and then transmits the counting end notification to the transmission suspension time management unit 1412.

In step S1712, the imaging execution unit 1408 determines whether the operator issues an instruction to execute the additional imaging operation while the transmission suspension time counting unit 1415 is counting a transmission suspension time. In other words, the imaging execution unit 1408 determines whether the operator issues an instruction to execute the additional imaging operation before the transmission suspension time management unit 1412 receives the counting end notification of the transmission suspension time. If the operator does not issue the instruction to execute the additional imaging operation (NO in step S1712), the imaging execution unit 1408 advances the processing to step S1713.

In step S1713, the transmission suspension time counting unit 1415 transmits the counting end notification to the inspection execution information management unit 1407 and the transmission unit 1416.

In step S1714, the inspection execution information management unit 1407 receives the counting end notification and then shifts the inspection state from the state where a transmission is suspended to the state where the inspection is ended. The transmission unit 1416 receives the counting end notification and then transmits the inspection end information and the image storage request to the intra-hospital information system 300. More specifically, the transmission unit 1416 transmits the inspection end notification to which the inspection end information is added to the inspection management system 307 and transmits the image storage request to the image storage and display apparatus 306 via the network.

The inspection execution information management unit 1407 updates the past inspection list displayed by the GUI on the display unit 11. More specifically, the inspection execution information management unit 1407 changes indication in the column of "inspection end information notification" of the inspection the state of which is shifted to the end state on the past inspection list to "Ended."

The image storage and display apparatus 306 receives the image storage request and then stores the image data received in step S1708. The inspection management system 307 receives the inspection end notification to which the inspection end information is added and manages the inspection end information in a database.

If the imaging execution unit 1408 determines that the operator issues the instruction to execute the additional imaging operation (YES in step S1712), the imaging execution unit 1408 issues an instruction to resume the inspection and returns the processing to step S1703. At this point, the inspection execution information management unit 1407 shifts the specified state of the inspection request information from the state where the transmission is suspended to the state where the inspection is being resumed. The flow of the inspection after resumption is similar to that in steps S1703 to S1711 described above.

In other words, if the processing proceeds to step S1707 after the inspection is resumed according to the instruction to execute the additional imaging operation, the inspection request information management unit 1406 generates updated inspection end information using the inspection execution information including the inspection added according to the instruction to execute the additional imaging operation. Incidentally, the inspection request information management unit 1406 may generate new inspection end information using the inspection execution information including the inspection added according to the instruction to execute the additional imaging operation.

In step S1708, the imaging execution unit 1408 transmits the image data acquired according to the instruction to execute the additional imaging operation to the image data management unit 1409. The image data management unit 1409 receives the image data and then storages the image data in the internal storage device 19 and transmits the image data to the transmission unit 1416. The transmission unit 1416 receives the image data and then directly transmits the image data to the image storage and display apparatus 306 via the network. For this reason, the operator can instantly examine the image data acquired according to the instruction to execute the additional imaging operation via the image storage and display apparatus 306.

In step S1710, the transmission suspension time management unit 1412 determines a transmission suspension time based on the inspection execution information including the inspection added according to the instruction to execute the additional imaging operation.

Thereafter, in step S1714, the transmission unit 1416 receives the counting end notification of the newly determined transmission suspension time and then transmits the updated inspection end information and the image storage request to the intra-hospital information system 300. If the inspection end information is newly generated based on the inspection added according to the instruction to execute the additional imaging operation, the transmission unit 1416 transmits the inspection end information generated before and after an imaging operation is added to the intra-hospital information system 300.

The resumption of the inspection according to the instruction to execute an additional imaging operation may be repeated over and over again until the counting of the transmission suspension time is ended. Thus, according to the present exemplary embodiment, the operator can instantly examine the image data acquired according to the instruction to execute the additional imaging operation via the image storage and display apparatus 306.

The operation processing for determining a transmission suspension time in the medical imaging apparatus according to the present exemplary embodiment is substantially similar to that in the flow chart of the first exemplary embodiment illustrated in FIG. 5, so that the description thereof is omitted. In other words, the imaging execution unit 404, the inspection management unit 407, and the transmission suspension time determination unit 405 according to the first exemplary embodiment correspond to the imaging execution unit 1408, the inspection execution information management unit 1407, and the transmission suspension time management unit 1412 according to the present exemplary embodiment, respectively. Furthermore, the index storage unit 403 and the index score setting unit 402 according to the first exemplary embodiment correspond to the index storage unit 1411 and the index score setting unit 1410 according to the present exemplary embodiment, respectively.

The GUI for the past inspection information list displayed on the display unit of the medical imaging apparatus according to the present exemplary embodiment is similar to that for the past inspection information list illustrated in FIG. 7 according to the first exemplary embodiment, so that the description thereof is omitted.

The operation processing of the medical imaging apparatus in instructing the inspection being in a transmission suspension state to execute the additional imaging operation according to the present exemplary embodiment is substantially similar to that in the flow chart of the first exemplary embodiment illustrated in FIG. 8, so that the description thereof is omitted. In other words, the imaging execution unit 404, the inspection management unit 407, the transmission suspension time determination unit 405, and the index storage unit 403 according to the first exemplary embodiment correspond to the index storage unit 1411, the imaging execution unit 1408, the inspection execution information management unit 1407, and the transmission suspension time management unit 1412 according to the present exemplary embodiment, respectively.

Furthermore, the index score setting unit 402, the "unit for counting the number of additional imaging operations for user 409," and the "unit for counting the number of additional imaging operations for patient" 410 according to the first exemplary embodiment correspond to the index score setting unit 1410, the "unit for counting the number of additional imaging operations for user 1413," and the "unit for counting the number of additional imaging operations for patient" 1414, respectively. The operation processing of the medical imaging apparatus in instructing the inspection being in a transmission suspension state to execute the additional imaging operation according to the present exemplary embodiment is different from that in step S1102 only of the first exemplary embodiment.

More specifically, in step S1102, the inspection execution information management unit 1407 shifts the state of the inspection request information instructed to execute the additional imaging operation by the operator from the state where the transmission is suspended to the state where the inspection is being resumed. Thus, the medical imaging apparatus according to the present exemplary embodiment can resume the inspection according to the instruction for the inspection being a transmission suspension state to execute the additional imaging operation.

The GUI for confirming or setting the index score used for determining the transmission suspension time and stored in the index storage unit 1411 is substantially similar to that according to the first exemplary embodiment illustrated in FIGS. 9, 10, and 11, so that the description thereof is omitted. In other words, the index storage unit 403 and the index score setting unit 402 according to the first exemplary embodiment correspond to the index storage unit 1411 and the index score setting unit 1410 according to the present exemplary embodiment, respectively.

The configuration and operation of a medical imaging apparatus according to a fifth exemplary embodiment of the present invention is described below. The fourth exemplary embodiment cannot cope with the case of a quick accounting because the inspection end notification is not transmitted unless the transmission suspension time elapses. The present exemplary embodiment described below is capable of conducting accounting with an inspection management system as required even in the transmission suspension state where the inspection end notification is not transmitted to the intra-hospital information system.

An internal configuration of the medical imaging apparatus according to the fifth exemplary embodiment is described below with reference to FIG. 18.

Figure 18:
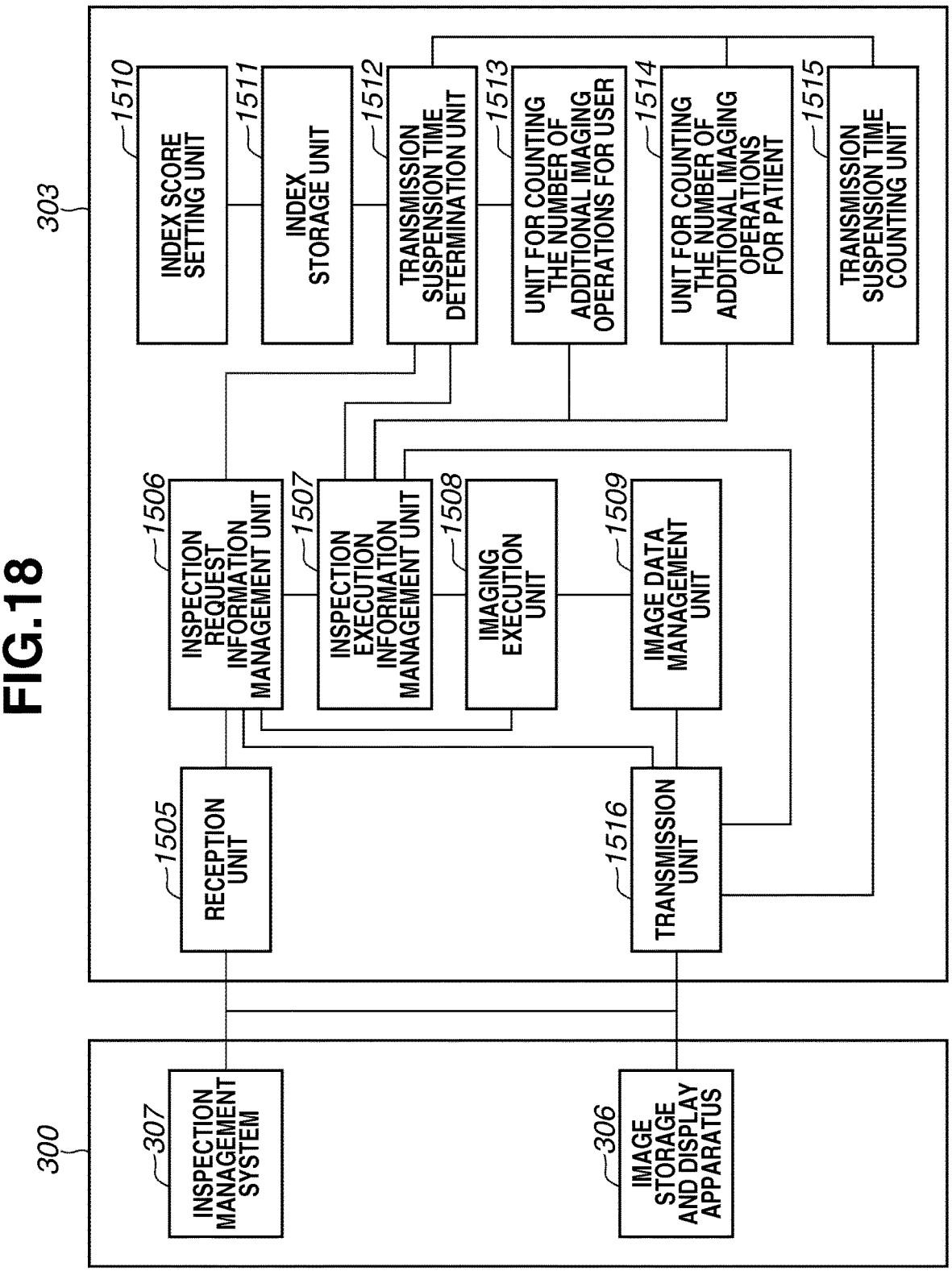
FIG. 18 is a block diagram illustrating an example of an internal configuration of a medical imaging apparatus according to a fifth exemplary embodiment of the present invention.

FIG. 18 is a block diagram illustrating an example of the internal configuration of the medical imaging apparatus. The medical imaging apparatus 303 according to the present exemplary embodiment is similar to that according to the fourth exemplary embodiment illustrated in FIG. 16. The components 1505 to 1516 of the medical imaging apparatus 303 illustrated in FIG. 18 correspond to the components 1405 to 1416 of the medical imaging apparatus 303 illustrated in FIG. 16 respectively.

In the fourth exemplary embodiment, the transmission suspension time for each inspection is determined and the inspection end notification and the image storage request are merely transmitted after counting is ended. In the present exemplary embodiment, however, the inspection end notification and the image storage request can be transmitted when accounting is desired to be performed with the inspection management system 307 irrespective of the state of the counting unless the inspection end notification and the image storage request are transmitted. Accordingly, in the present exemplary embodiment, the reception unit 1505 receives not only the inspection request information but also the accounting request transmitted from the inspection management system 307.

The operation processing of the medical imaging apparatus according to the present exemplary embodiment is described below with reference to FIG. 19.

Figure 19:
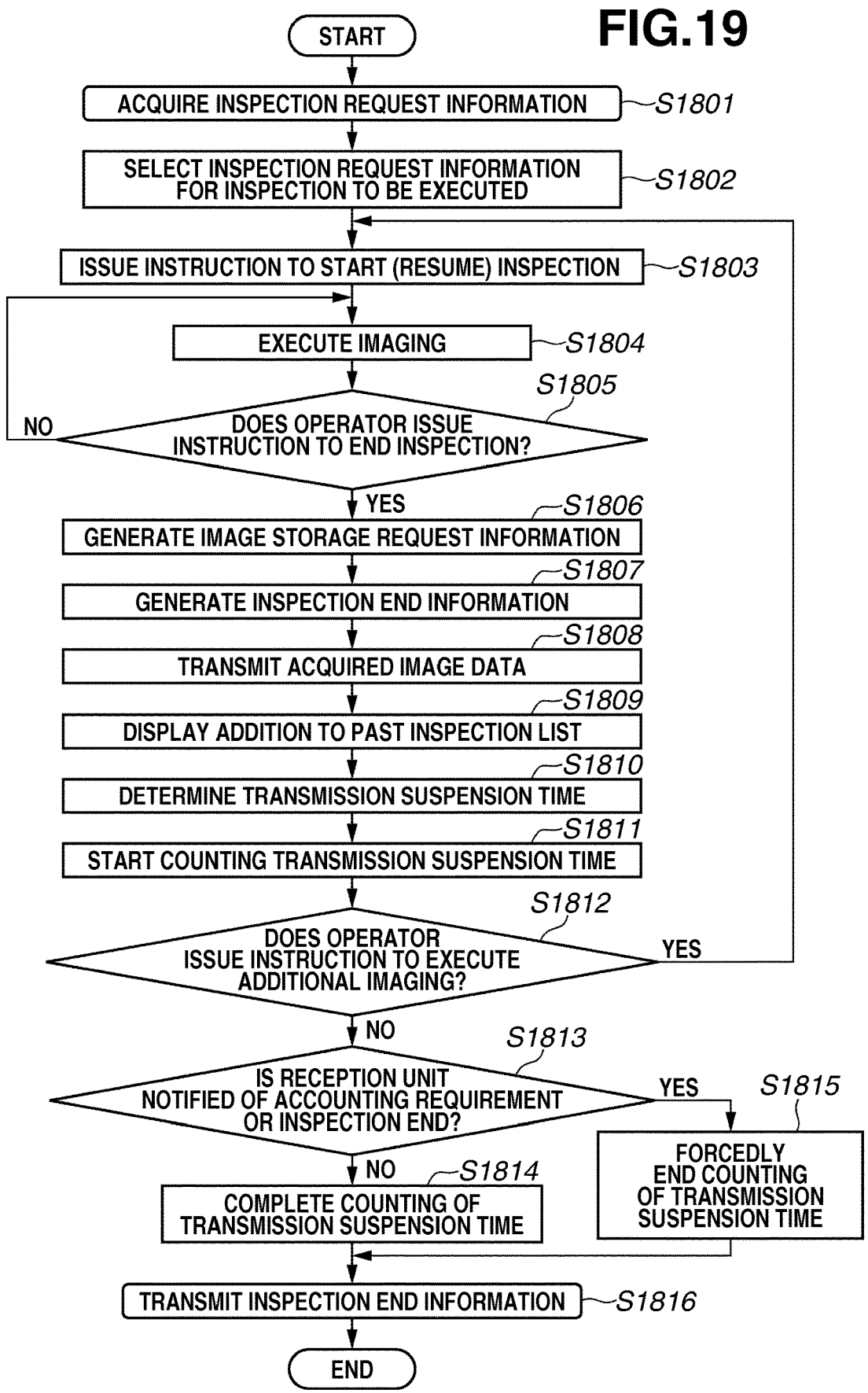
FIG. 19 is a flow chart illustrating an example of the operation processing of the medical imaging apparatus according to the fifth exemplary embodiment.

FIG. 19 is a flow chart illustrating an example of the operation processing performed from the time of reception of the inspection request information to the time of transmission of the inspection end notification. The processing is implemented by the CPU 18 of the medical imaging apparatus 303 executing the program stored in the ROM 16.

Steps S1801 to S1812 in the flow chart illustrated in FIG. 19 are similar to steps S1701 to S1712 in the fourth exemplary embodiment. For this reason, the processing only in step S1813 and following steps is described.

In step S1813, the reception unit 1505 determines whether the inspection management system 307 transmits the accounting request to the reception unit 1505 while the transmission suspension time counting unit 1515 is counting the transmission suspension time. If the inspection management system 307 transmits the accounting request to the reception unit 1505 (YES S1813), the processing proceeds to step S1815.

In step S1815, the reception unit 1505 receives the accounting request from the inspection management system 307. The reception unit 1505 receives the accounting request and then transmits the accounting request to the transmission suspension time management unit 1512 via the inspection execution information management unit 1507. The transmission suspension time management unit 1512 receives the accounting request and then confirms that the inspection of which accounting is requested is in the transmission suspension state. After the confirmation, the transmission suspension time management unit 1512 notifies the transmission suspension time counting unit 1515 of the instruction to end counting. The inspection execution information management unit 1507 shifts the state of the inspection of which accounting is requested from a transmission suspension state to an end state. The transmission suspension time counting unit 1515 is instructed to end counting and then ends the counting of the transmission suspension time of the inspection subjected to the instruction. The inspection request information management unit 1506 instructs the transmission unit 1516 to transmit the inspection end notification, the inspection end information, and the image storage request.

In step S1816, the inspection execution information management unit 1507 is instructed to end counting and then shifts the state of the inspection from the transmission suspension state to the end state. The transmission unit 1516 is instructed to transmit the inspection end notification, the inspection end information, and the image storage request and then transmits the inspection end notification to which the inspection end information is added to the inspection management system 307 and transmits the image storage request to the image storage and display apparatus 306.

The inspection execution information management unit 1507 updates the past inspection list displayed by the GUI on the display unit 11. More specifically, the inspection execution information management unit 1507 changes indication in the column of "inspection end information notification" of the inspection the state of which is shifted to the end state in the past inspection list to "Ended."

In step S1813, if the reception unit 1505 does not receive the accounting request (NO in step S1813), the processing proceeds to step S1814. The processing in step 1814 is similar to that in step S1713 of the flow chart illustrated in FIG. 17 according to the first exemplary embodiment, so that the description thereof is omitted.

In the present exemplary embodiment, the resumption of the inspection according to the instruction to execute an additional imaging operation may be repeated over and over again until the counting of the transmission suspension time is ended or the accounting request is transmitted from the inspection management system 307.

Thus, according to the present exemplary embodiment, if the inspection management system 307 notifies the reception unit 1505 of the accounting request, the transmission suspension time counting unit 1515 ends the counting of transmission suspension time and the transmission unit 1516 transmits the inspection end notification to which the inspection end information is added to the inspection management system 307. For this reason, the inspection management system 307 can quickly perform accounting.

In the above description, in step S1813, the reception unit 1505 determines whether the inspection management system 307 transmits the accounting request to the reception unit 1505. In another alternative, in step S1813, for example, the reception unit 1505 may determine whether the image storage and display apparatus 306 transmits an image examination end notification to the reception unit 1505. In other words, the operator examines the image data via the image storage and display apparatus 306 and if the operator determines that there is no need for adding an imaging operation, the operator issues an instruction to end the examination of an image via the input unit of the image storage and display apparatus 306. The image storage and display apparatus 306 transmits the image examination end notification to the medical imaging apparatus 303 and the reception unit 1505 receives the image examination end notification. The processing in subsequent steps 1815 and 1816 is similar to the processing described above. Thus, in the case where the operator does not issue an instruction to add an imaging operation, the inspection management system 307 can quickly perform accounting.

The configuration and operation of a medical imaging apparatus according to a sixth exemplary embodiment of the present invention is described below. In the fourth and fifth exemplary embodiments, if the operator turns off the power supply of the medical imaging apparatus in the transmission suspension state where the inspection end notification is not transmitted to the inspection management system, the inspection end notification remains untransmitted, so that the inspection management system cannot perform post-processing. In the present exemplary embodiment, even if the operator turns off the power supply of the medical imaging apparatus in the transmission suspension state where the inspection end notification is not transmitted to the intra-hospital information system, the inspection end notification can be transmitted to the intra-hospital information system.

An internal configuration of the medical imaging apparatus according to the sixth exemplary embodiment is described below with reference to FIG. 20.

Figure 20:
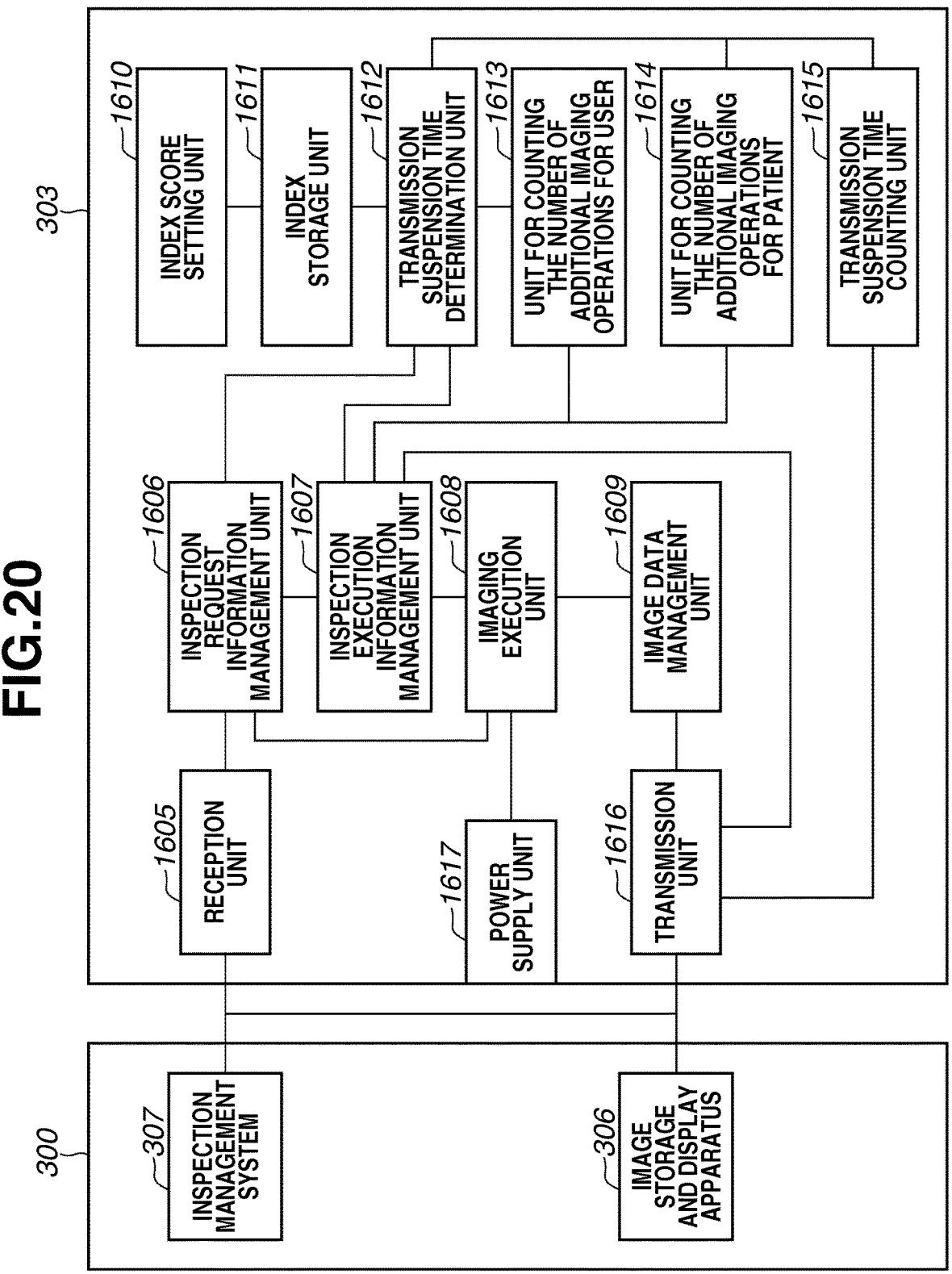
FIG. 20 is a block diagram illustrating an example of an internal configuration of a medical imaging apparatus according to a sixth exemplary embodiment of the present invention.

FIG. 20 is a block diagram illustrating an example of the internal configuration of the medical imaging apparatus. The medical imaging apparatus 303 according to the present exemplary embodiment is substantially similar in configuration to that in the fourth exemplary embodiment illustrated in FIG. 16, but different from the fourth exemplary embodiment in that the medical imaging apparatus 303 includes a power supply unit 1617. The components 1605 to 1616 of the medical imaging apparatus 303 illustrated in FIG. 20 correspond to the components 1405 to 1416 of the medical imaging apparatus 303 illustrated in FIG. 16.

The power supply unit 1617 is attached to the medical imaging apparatus 303 and turns on and off the medical imaging apparatus 303. When the power supply unit 1617 switches the medical imaging apparatus 303 from the on state to the off state, the power supply unit 1617 transmits a power supply OFF notification to the inspection execution information management unit 1607 via the imaging execution unit 1608. The inspection execution information management unit 1607 receives the power supply OFF notification and then causes the transmission unit 1616 to transmit the inspection end notification, the inspection end information, and the image storage request of the inspection in the transmission suspension state to the intra-hospital information system 300.

Figure 21:
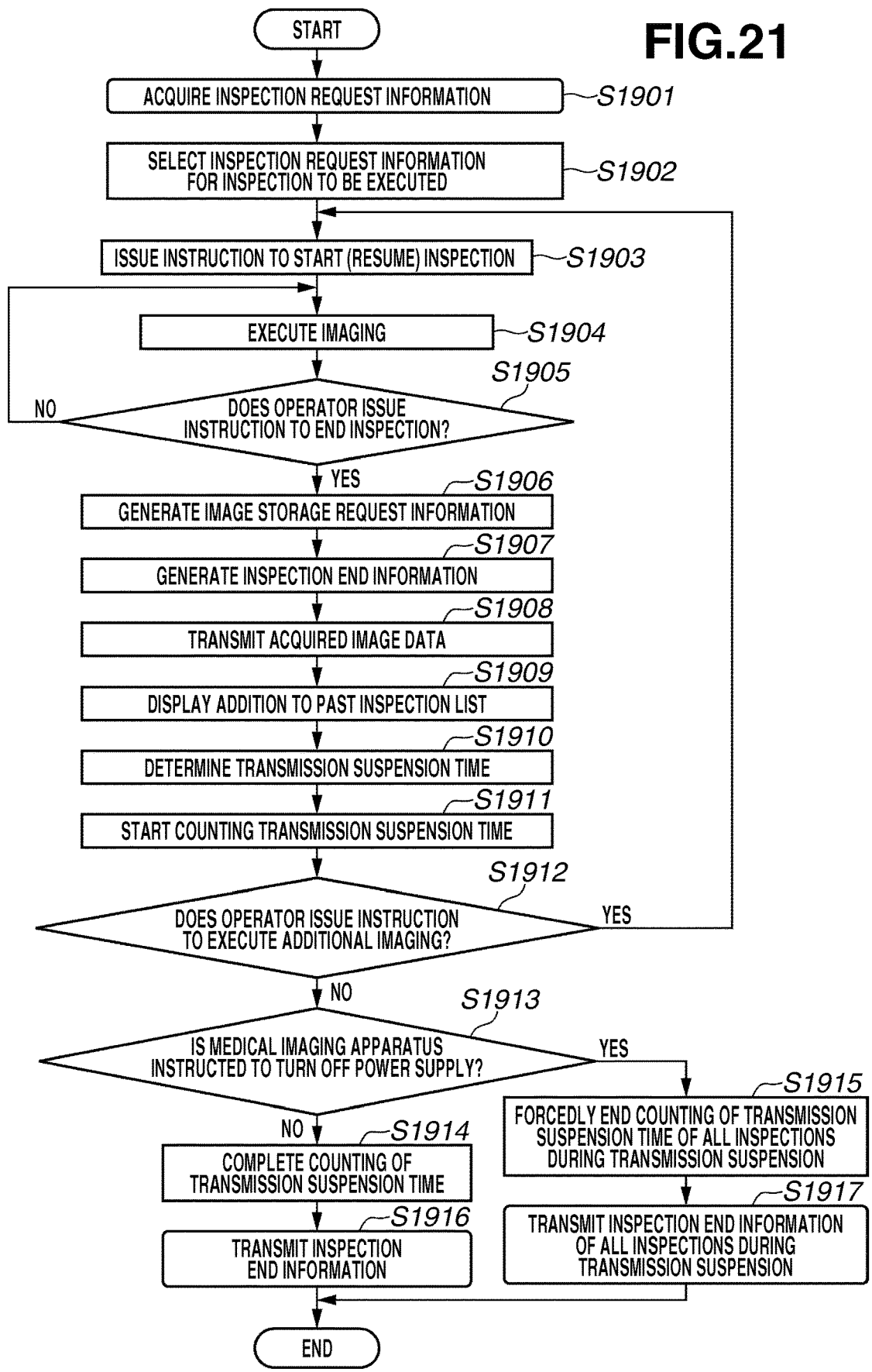
FIG. 21 is a flow chart illustrating an example of the operation processing of the medical imaging apparatus according to the sixth exemplary embodiment.

The operation processing of the medical imaging apparatus according to the present exemplary embodiment is described below with reference to FIG. 21. FIG. 21 is a flow chart illustrating an example of the operation processing performed from the time of reception of the inspection request information to the time of transmission of the inspection end notification. The processing is implemented by the CPU 18 of the medical imaging apparatus 303 executing the program stored in the ROM 16.

Steps S1901 to S1912 in the flow chart illustrated in FIG. 21 are similar to steps S1701 to S1712 in the fourth exemplary embodiment. For this reason, the processing only in step S1913 and following steps is described.

In step S1913, the power supply unit 1617 determines whether the operator issues an instruction to turn off the power supply of the medical imaging apparatus 303 while the transmission suspension time counting unit 1615 is counting a transmission suspension time. If the operator issues the instruction to turn off the power supply (YES in step S1913), the processing proceeds to step S1915.

In step S1915, the power supply unit 1617 transmits the power supply OFF notification to the inspection execution information management unit 1607 via the imaging execution unit 1608 before turning off the power supply. The inspection execution information management unit 1607 receives the power supply OFF notification and then issues an instruction to end counting to the transmission suspension time counting unit 1615 via the transmission suspension time management unit 1612. At this point, the inspection execution information management unit 1607 shifts the state of all inspections being in the transmission suspension state from the transmission suspension state to the end state. The transmission suspension time counting unit 1615 receives the instruction to end counting and then ends the counting of the transmission suspension time of the inspection subjected to the instruction.

In step S1917, the inspection execution information management unit 1607 instructs the transmission unit 1616 to transmit the inspection end notification, the inspection end information, and the image storage request of all inspections rendered to the end state for each inspection to the transmission unit 1616. The transmission unit 1616 receives the instruction for transmission and then transmits the inspection end notification to which the inspection end information is added to the inspection management system 307 and transmits the image storage request information to the image storage and display apparatus 306.

The transmission unit 1616 confirms that the inspection end notification of all inspections is transmitted and then transmits the transmission end notification to the power supply unit 1617 via the inspection execution information management unit 1607 and the imaging execution unit 1608. The power supply unit 1617 receives the transmission end notification and then turns off the power supply of the medical imaging apparatus 303.

The inspection execution information management unit 1607 updates the past inspection list displayed by the GUI on the display unit 11. More specifically, the inspection execution information management unit 1607 changes indication in the column of "inspection end information notification" of the inspection the state of which is shifted to the end state in the past inspection list to "Ended."

On the other hand, if the power supply unit 1617 does not determine that the operator issues an instruction to turn off the power supply (NO in step S1913), the processing proceeds to steps S1914 and S1916. The processing in steps S1914 and S1916 is similar to that in steps S1713 and S1714 of the flow chart of the fourth exemplary embodiment illustrated in FIG. 17, so that the description thereof is omitted.

The flow chart illustrated in FIG. 21 describes the case where the timing at which the operator issues the instruction to turn off the power supply of the medical imaging apparatus 303 is determined after the processing in step S1912, but the timing is not limited to this case. In other words, irrespective of the timing at which the operator issues the instruction, the power supply unit 1617 determines that the operator issues the instruction to turn off the power supply of the medical imaging apparatus 303, and thereafter, the processing proceeds to steps S1915 and S1917 and the aforementioned processing is performed.

In the present exemplary embodiment, the resumption of the inspection according to the instruction to execute an additional imaging operation may be repeated over and over again until the counting of the transmission suspension time is ended or the power supply of the medical imaging apparatus 303 is turned off.

Thus, according to the present exemplary embodiment, even if the power supply of the medical imaging apparatus 303 is turned off, the inspection end notification of the inspection being in the transmission suspension state is transmitted to the intra-hospital information system 300 to allow preventing the inspection end notification from not being transmitted.

According to the present exemplary embodiment, the transmission suspension time during which the inspection end notification to which the inspection request information is added and the image storage request are transmitted to the intra-hospital information system after the inspection performed by the medical imaging apparatus is ended can be set for each inspection based on inspection information. Accordingly, even in the case where an imaging operation is added to the inspection once ended, for example, there is no need for performing re-inspection by acquiring again the inspection request information, allowing readily adding an imaging operation, which improves the operability of the operator and reduces the patient's burden.

Furthermore, according to the present exemplary embodiment, the image data acquired by the medical imaging apparatus is transmitted independently of the transmission suspension time at the timing at which the inspection is ended, which enables the operator to accurately examine the image after the inspection is ended using a high definition monitor of the image storage and display apparatus. If an imaging operation is required to be added as a result of examining the image, the imaging operation can be easily added if it is in the transmission suspension time. Consequently, it is advantageous, as the operator's measure for adding an imaging operation, to determine the inspection in which an imaging operation is probably required to be added after the inspection is ended using inspection information from the viewpoint of complicatedness and to set the transmission suspension time.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. An imaging information processing apparatus comprising:
   an inspection end information generation unit configured to generate inspection end information including a content related to an imaging operation executed in an inspection;
   an inspection end information transmission unit configured to transmit the inspection end information to an intra-hospital information system when a transmission suspension time passes after an instruction to end the inspection is received;
   an index setting unit configured to set at least one of information from among inspection request information, inspection execution information, information about a patient to be inspected, information about the number of additional user imaging operations for each operator, and information about the number of additional patient imaging operations for each patient, according to selection by an operator, as inspection information based on which transmission suspension time is determined; and
   transmission suspension time determination unit configured to determine a transmission suspension time based on at least one of information from among the inspection request information, the inspection execution information, the information about a patient to be inspected, the information about the number of additional user imaging operations for each operator, and the information about the number of additional patient imaging operations for each patient set by the index setting unit as the inspection information,
   wherein the inspection end information generation unit is configured to generate inspection end information including a content related to an additional imaging operation in a case where the additional imaging operation is executed during a period from when the instruction to end the inspection is received to when the transmission suspension time passes, and
   wherein the inspection end information transmission unit is configured to transmit the inspection end information including the content related to the additional imaging operation to the intra-hospital information system.

2. The imaging information processing apparatus according to claim 1, wherein the transmission suspension time determination unit is configured to determine the transmission suspension time based on a score and a weighting coefficient set to index items of each of the inspection request information, the inspection execution information, the information about the patient to be inspected, the information about the number of additional user imaging operations for each operator, and the information about the number of additional patient imaging operations for each patient.

3. The imaging information processing apparatus according to claim 1, wherein
   the index setting unit is configured to change a score and a weighting coefficient set to index items of each of the inspection request information, the inspection execution information, the information about the patient to be inspected, the information about the number of additional user imaging operations for operator, and the information about the number of additional patient imaging operations for patient, according to setting by the operator.

4. The imaging information processing apparatus according to claim 1, wherein
   the index setting unit is configured to perform setting so that the transmission suspension time determination unit determines a uniform transmission suspension time for all inspections, according to the setting by the operator.

5. The imaging information processing apparatus according to claim 1, further comprising a transmission suspension time counting unit configured to count the transmission suspension time after the instruction to end the inspection is received,
   wherein the transmission suspension time counting unit is configured to reset counting of the transmission suspension time in a case where the additional imaging operation is executed.

6. The imaging information processing apparatus according to claim 1, further comprising an accounting request determination unit configured to determine whether an accounting request is received from the intra-hospital information system,
   wherein, in a case where the accounting request determination unit determines that the accounting request is received, the inspection end information transmission unit transmits the inspection end information generated by the inspection end information generation unit to the intra-hospital information system before the transmission suspension time passes.

7. The imaging information processing apparatus according to claim 1, further comprising a power supply turning-off instruction determination unit configured to determine whether a power supply turning-off instruction is received from the operator,
   wherein, in a case where the power supply turning-off instruction determination unit determines that the power supply turning-off instruction is received, the inspection end information transmission unit transmits the inspection end information generated by the inspection end information generation unit to the intra-hospital information system before the transmission suspension time passes.

8. The imaging information processing apparatus according to claim 1, further comprising an image data transmission unit configured to transmit image data acquired in the imaging operation to the intra-hospital information system, wherein, in a case where the additional imaging operation is executed, the image data transmission unit transmits the image data acquired in the additional imaging operation.

9. The imaging information processing apparatus according to claim 8, wherein the image data transmission unit is configured to transmit the image data acquired in the imaging operation to an image display apparatus as the intra-hospital information system before the transmission suspension time passes.

10. The imaging information processing apparatus according to claim 9, further comprising an image-examination end notification determination unit configured to determine whether an image-examination end notification is received from the image display apparatus,
wherein, in a case where the image-examination end notification determination unit determines that the image-examination end notification is received, the inspection end information transmission unit transmits the inspection end information generated by the inspection end information generation unit to the intra-hospital information system before the transmission suspension time passes.

11. A control method of controlling an imaging processing apparatus, the control method comprising:
generating inspection end information including a content related to an imaging operation executed in an inspection, by an inspection end information generation unit of the imaging processing apparatus;
transmitting the inspection end information to an intra-hospital information system when a transmission suspension time passes after an instruction to end the inspection is received, by an inspection end information transmission unit of the imaging processing apparatus;
setting at least one of information from among inspection request information, inspection execution information, information about a patient to be inspected, information about the number of additional user imaging operations for each operator, and information about the number of additional patient imaging operations for each patient, according to selection by an operator, as inspection information based on which transmission suspension time is determined, by an index setting unit of the imaging processing apparatus; and
determining, by a transmission suspension time determination unit of the imaging processing apparatus, a transmission suspension time based on at least one of information from among the inspection request information, the inspection execution information, the information about a patient to be inspected, the information about the number of additional user imaging operations for each operator, and the information about the number of additional patient imaging operations for each patient set by the index setting unit as the inspection information,
wherein, in the generating the inspection end information, the inspection end information generation unit is configured to generate inspection end information including a content related to an additional imaging operation in a case where the additional imaging operation is executed during a period from when the instruction to end the inspection is received to when the transmission suspension time passes, and
wherein, in the transmitting the inspection end information, the inspection end information transmission unit is configured to transmit the inspection end information including the content related to the additional imaging operation to the intra-hospital information system.

12. A non-transitory computer-readable storage medium storing a program for causing an imaging processing apparatus to function as:
an inspection end information generation unit configured to generate inspection end information including a content related to an imaging operation executed in an inspection;
an inspection end information transmission unit configured to transmit the inspection end information to an intra-hospital information system when a transmission suspension time passes after an instruction to end the inspection is received;
an index setting unit configured to set at least one of information from among inspection request information, inspection execution information, information about a patient to be inspected, information about the number of additional user imaging operations for each operator, and information about the number of additional patient imaging operations for each patient, according to selection by an operator, as inspection information based on which transmission suspension time is determined; and
transmission suspension time determination unit configured to determine a transmission suspension time based on at least one of information from among the inspection request information, the inspection execution information, the information about a patient to be inspected, the information about the number of additional user imaging operations for each operator, and the information about the number of additional patient imaging operations for each patient set by the index setting unit as the inspection information,
wherein the inspection end information generation unit is configured to generate inspection end information including a content related to an additional imaging operation in a case where the additional imaging operation is executed during a period from when the instruction to end the inspection is received to when the transmission suspension time passes, and
wherein the inspection end information transmission unit is configured to transmit the inspection end information including the content related to the additional imaging operation to the intra-hospital information system.

* * * * *